(12) United States Patent
Zichi et al.

(10) Patent No.: US 11,965,880 B2
(45) Date of Patent: Apr. 23, 2024

(54) NEXT-GENERATION SEQUENCING FOR PROTEIN MEASUREMENT

(71) Applicant: SomaLogic Operating Co., Inc., Boulder, CO (US)

(72) Inventors: Dom Zichi, Boulder, CO (US); Allison Weiss, Boulder, CO (US); David Seghetti, Boulder, CO (US); Kathryn Jenko, Denver, CO (US)

(73) Assignee: SomaLogic Operating Co., Inc., Boulder, CO (US)

( * ) Notice: Subject to any disclaimer, the term of this patent is extended or adjusted under 35 U.S.C. 154(b) by 79 days.

(21) Appl. No.: 18/148,350

(22) Filed: Dec. 29, 2022

(65) Prior Publication Data

US 2023/0213502 A1    Jul. 6, 2023

Related U.S. Application Data

(60) Provisional application No. 63/294,964, filed on Dec. 30, 2021.

(51) Int. Cl.
*C12N 15/10* (2006.01)
*G01N 33/53* (2006.01)

(52) U.S. Cl.
CPC ..... *G01N 33/5308* (2013.01); *C12N 15/1048* (2013.01)

(58) Field of Classification Search
CPC .......................... G01N 33/5308; C12N 15/1048
See application file for complete search history.

(56) References Cited

U.S. PATENT DOCUMENTS

2020/0058369 A1    2/2020    Kim
2020/0087707 A1    3/2020    Engreitz

FOREIGN PATENT DOCUMENTS

WO    2005108609 A1    11/2005

OTHER PUBLICATIONS

Kraemer et al. PLoS One. 2011. 6(10):e26332. (Year: 2011).*
Yoshida et al. Expert Review of Molecular Diagnostics. 2014. 14(2):L143-151. (Year: 2014).*
Gold et al. New Biotechnology. 2012. 29(5):543-549. (Year: 2012).*
Turner et al. Anal Chem. 2011. 83:666-670. (Year: 2011).*
Wik, Lotta, et al.; "Proximity Extension Assay in Combination with Next-Generation Sequencing for High-throughput Proteome-wide Analysis," Technological Innovation and Resources, Mol Cell Proteomics, vol. 20, 100168, 2021.
Olink Proteomics Ab; "PEA—a high-multiplex immunoassay technology with qPCR or NGS readout," Olink Proteomics AB, 1129, v1.0, May 26, 2020.

(Continued)

*Primary Examiner* — Joseph G. Dauner
(74) *Attorney, Agent, or Firm* — Kolitch Romano Dascenzo Gates LLC

(57) ABSTRACT

Methods of detecting and quantifying target molecules, such as proteins, in a biological sample are provided. The disclosed methods include capturing target molecules with aptamers, replacing the aptamers with aptamer identification sequences, and then sequencing the aptamer identification sequences using next-generation sequencing techniques.

22 Claims, 14 Drawing Sheets

(56) References Cited

OTHER PUBLICATIONS

Baumstummler, Specific Capture and Detection of *Staphylococcus aureus* With High-Affinity Modified Aptamers To Cell Surface Components, Letters In Applied Microbiology, vol. 59, pp. 422-431, John Wiley & Sons Ltd, 2014.
International Search Report and Written Opinion for application PCT/US22/82594 dated Mar. 31, 2023.

* cited by examiner

NEXT-GENERATION SEQUENCING FOR PROTEIN MEASUREMENT

CROSS-REFERENCES

The following applications and materials are incorporated herein, in their entireties, for all purposes: U.S. Provisional Patent Application Ser. No. 63/294,964, filed Dec. 30, 2021.

FIELD

This disclosure relates to systems and methods for quantitative measurement of proteins in a biological sample. More specifically, the disclosed embodiments relate to capturing target proteins with specifically designed aptamers, creating an eluate of aptamers that captured target proteins, and then replacing the aptamers in the eluate with "reporter" DNA molecules that can be sequenced more easily than the aptamers themselves.

INTRODUCTION

Conventionally, various attempts to evaluate genetic activity and/or decode biological processes, including disease processes or biological processes of pharmacological effect, have been focused on genomics. However, proteomics can provide further information about the biological function of cells and organisms. Proteomics includes qualitative and quantitative measurement of gene activity by detecting and quantifying the expression on a protein level rather than the genetic level. Proteomics also includes a study of events which are not coded genetically, such as a post-translational modification of proteins and interactions between proteins.

At present, it is possible to obtain an enormous volume of genome information. DNA chips have come into practical use as molecular arrays for this purpose and the price of direct DNA sequencing has continued to drop significantly. Likewise, there is an increasing demand for high throughput proteomics. Proteomics is far preferable to genomics for the monitoring of health, as the genome is static, indicating only medical potential, while the proteome varies dynamically with a patient's medical state, and may even be said to define their medical state. However, detecting and quantitating proteins is hard, while detecting and quantitating nucleic acids is relatively easy, at least in part because proteins are more complicated and more variable in biological functions than DNA. This has motivated many efforts to measure mRNA (messenger RNA) concentrations as a proxy for protein concentrations. However, mRNA concentrations have been shown not to correlate well with protein concentrations. It appears that proteomics relies on the ability to detect proteins directly.

One way to detect and quantify the presence of specific proteins in a biological sample is through the use of protein-capture SOMAmer® (Slow Off-rate Modified Aptamer) reagents. SOMAmer reagents are constructed with chemically modified nucleotides that greatly expand the physicochemical diversity of the large randomized nucleic acid libraries from which the SOMAmer reagents are selected. An assay using SOMAmer reagents measures native proteins in complex matrices by transforming each individual protein concentration into a corresponding SOMAmer reagent concentration, which is then quantified by standard DNA techniques such as microarrays or qPCR.

SOMAmer reagents are single stranded DNA-based protein affinity reagents that include chemically modified nucleotides which mimic amino acid side chains, expanding the chemical diversity of standard aptamers and enhancing the specificity and affinity of protein-nucleic acid interactions. These modified nucleotides are incorporated into nucleic acid libraries used for the iterative selection and amplification process called SELEX (Systematic Evolution of Ligands by EXponential enrichment) from which SOMAmer reagents are selected. Using a SELEX-type process, SOMAmer reagents can be generated to capture proteins that had been resistant to selection with unmodified nucleic acids (ACTG traditional aptamers). SOMAmer reagents can be tailored to select for the desirable properties of specificity and slow off-rate, as well as to mimic the assay conditions under which the reagents will be used.

In SOMAmer-based assays, the presence of proteins in a sample is transformed into a specific SOMAmer-based DNA signal. A SOMAmer-protein binding step is followed by a series of partitioning and wash steps that converts relative protein concentrations into measurable nucleic acid signals that are quantified using DNA detection technology, such as by hybridization of fluorophore-labeled SOMAmers to custom DNA microarrays. Upon laser scanning the microarray, the readout in relative fluorescent units (RFU) is directly proportional to the amount of target protein in the initial sample.

Quantifying protein detection using microarray hybridization has various drawbacks. These include limited scalability, fixed assay costs, and limited commercial sources for the microarrays. Accordingly, it is desirable to develop alternative methods of quantifying SOMAmer molecules in a post-capture eluate.

SUMMARY

The present disclosure provides systems, apparatuses, and methods relating to detection and quantification of proteins using a parallel sequencing technology known as next-generation sequencing or NGS. More specifically, the present disclosure relates to hybridization-capture (HC) techniques in which SOMAmer eluate molecules signaling protein capture are replaced by "reporter" DNA molecules containing SOMAmer-specific identification tags or "SOMA IDs" that may then be sequenced using NGS technology.

In some embodiments, the present disclosure relates to systems and methods for quantifying the abundances of target proteins in a biological sample, comprising capturing the target proteins by exposing the biological sample to a plurality of aptamers each configured to bind to a specific protein; isolating the aptamers that captured one of the target proteins in an aptamer-containing eluate; forming a plurality of tri-molecular complexes by exposing the aptamers in the eluate to a plurality of capture probes each configured to hybridize to a particular aptamer, each tri-molecular complex including one of the aptamers from the eluate, a first capture probe including a portion hybridized to a first portion of the aptamer, and a second capture probe including a portion hybridized to a second portion of the aptamer, a DNA primer region, and an aptamer ID sequence corresponding to the aptamer; separating the tri-molecular complexes from capture probes not bound to aptamers; dissociating the capture probes in the tri-molecular complexes from the corresponding aptamers; amplifying the aptamer ID sequences in the dissociated capture probes; sequencing the aptamer ID sequences via next-generation sequencing; and based on data obtained by sequencing the aptamer ID sequences, determining the abundances of the target proteins in the biological sample.

In some embodiments, the present disclosure relates to systems and methods for quantifying the abundances of two or more species of target proteins in a biological sample, comprising capturing the target proteins by exposing the biological sample to a plurality of aptamers each configured to capture a specific protein; forming an aptamer-containing eluate by isolating the aptamers that captured one of the target proteins in the biological sample; forming a plurality of tri-molecular complexes, each including a particular aptamer present in the aptamer-containing eluate, a first probe hybridized to a corresponding first portion of the particular aptamer, and a second probe including a portion hybridized to a corresponding second portion of the particular aptamer, at least one DNA primer region, and an aptamer ID sequence corresponding to the particular aptamer; amplifying the aptamer ID sequences; sequencing the aptamer ID sequences; and based on the sequenced aptamer ID sequences, quantifying the abundances of the target proteins.

In some embodiments, the present disclosure relates to systems and methods for detecting a target protein in a biological sample, comprising capturing the target protein with an aptamer by combining the biological sample with a plurality of aptamers each configured to capture a specific protein; forming a tri-molecular complex including the aptamer that captured the target protein, a first probe including a portion hybridized to a corresponding first portion of the aptamer that captured the target protein, and a second probe including a portion hybridized to a corresponding second portion of the aptamer that captured the target protein, at least one DNA primer region, and an aptamer ID sequence corresponding to the aptamer that captured the target protein; amplifying the aptamer ID sequence; and sequencing the aptamer ID sequence to identify the aptamer ID sequence thereby identifying the aptamer that captured the target protein and the target protein.

In some embodiments according to aspects of the present disclosure, aptamers used to capture target proteins may be sequenced directly, e.g. using next-generation sequencing techniques, without the use of tri-molecular complexes to transform the aptamers into simpler sequences.

In some embodiments according to aspects of the present disclosure, aptamers used to capture target proteins may be SOMAmers.

In some embodiments according to aspects of the present disclosure, an aptamer-containing eluate may be divided into groups before and/or after exposure to hybridized probe regions. In some cases, some or all of the eluate groups may be diluted to a desired degree.

In some embodiments according to aspects of the present disclosure, a quantitative spike reporter may be added at a desired assay stage, to correct compensatory changes in analyte counting proportionality.

Features, functions, and advantages may be achieved independently in various embodiments of the present disclosure, or may be combined in yet other embodiments, further details of which can be seen with reference to the following description and drawings.

DETAILED DESCRIPTION

Figure 1:
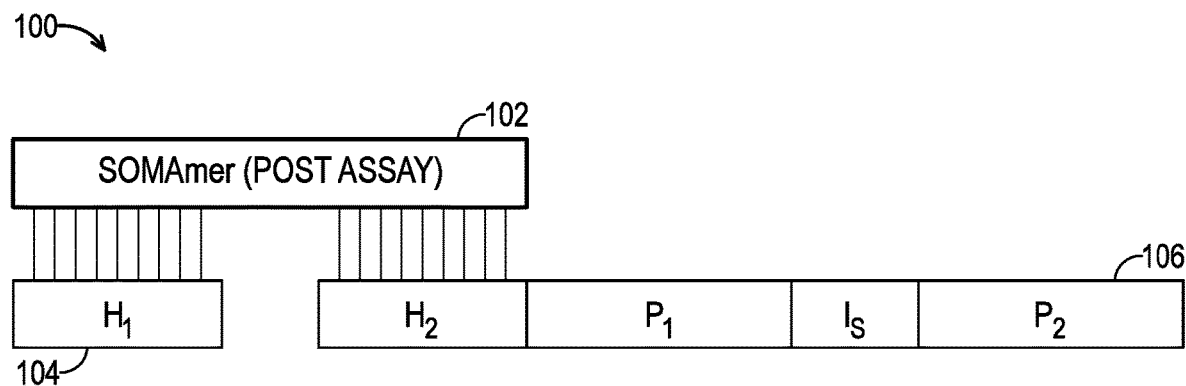
FIG. 1 is a schematic depiction of a tri-molecular complex including an aptamer and two probes hybridized to the aptamer, in accordance with aspects of the present disclosure.

Various aspects and examples of a hybridization-capture, next-generation sequencing assay system for protein detection and quantification, as well as related methods, are described below and illustrated in the associated drawings. Unless otherwise specified, a protein assay in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Advantages, Features, and Benefits; and (5) Conclusion. The Examples, Components, and Alternatives section is further divided into subsections, each of which is labeled accordingly.

Definitions

The following definitions apply herein, unless otherwise indicated.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

Directional terms such as "up," "down," "vertical," "horizontal," and the like should be understood in the context of the particular object in question. For example, an object may be oriented around defined X, Y, and Z axes. In those examples, the X-Y plane will define horizontal, with up being defined as the positive Z direction and down being defined as the negative Z direction.

"Providing," in the context of a method, may include receiving, obtaining, purchasing, manufacturing, generating, processing, preprocessing, and/or the like, such that the object or material provided is in a state and configuration for other steps to be carried out.

"NGS" refers to "next-generation sequencing."

"HC" means "hybridization capture."

"SOMAmer" refers to "Slow Off-rate Modified Aptamer" reagents developed and manufactured by SomaLogic Operating Co., Inc. of Boulder, Colorado ("SomaLogic").

"SOMAmer ID sequence" or "SOMA ID" or "reporter" refers to a portion of a tri-molecular complex including a SOMAmer-specific DNA strand that can be sequenced using NGS techniques.

"Quantitative spike" or "reporter spike" or "qSpike" refers to amplifiable reporters that are used to normalize compensatory read counts across samples, allowing true signal changes to be discerned.

In this disclosure, one or more publications, patents, and/or patent applications may be incorporated by reference.

However, such material is only incorporated to the extent that no conflict exists between the incorporated material and the statements and drawings set forth herein. In the event of any such conflict, including any conflict in terminology, the present disclosure is controlling.

Overview

In general, the present disclosure relates to methods of detecting and quantifying target molecules, such as proteins, in a biological sample. The disclosed methods may include capturing target molecules with aptamers, replacing the aptamers with aptamer identification sequences, and then sequencing the aptamer identification sequences using next-generation sequencing techniques. Alternatively, the disclosed methods may include capturing target molecules with aptamers followed by direct sequencing of the aptamers.

Examples, Components, and Alternatives

The following sections describe selected aspects of protein detection and quantification using aptamers such as SOMAmer reagents, where the SOMAmers are replaced via hybridization capture by reporter DNA molecules containing SOMAmer-specific segments which can be sequenced using next-generation sequencing techniques, as well as related systems and/or methods. The examples in these sections are intended for illustration and should not be interpreted as limiting the scope of the present disclosure. Each section may include one or more distinct embodiments or examples, and/or contextual or related information, function, and/or structure.

A. Illustrative Aptamers

This section describes SOMAmers (Slow Off-rate Modified Aptamers), which are illustrative examples of an aptamer suitable use in conjunction with example systems and methods described herein.

Through a method known as "Systematic Evolution of Ligands by EXponential enrichment," sometimes termed the SELEX process, it has become clear that nucleic acids have three-dimensional structural diversity not unlike proteins. The SELEX process is a method for the in vitro evolution of nucleic acid molecules for a certain desired activity. Here we describe SELEX for generating nucleic acid molecules with highly specific binding to target molecules. The SELEX process provides a class of products which are referred to as nucleic acid ligands or aptamers, each having a unique sequence, and having the property of binding specifically to a desired target compound or molecule. Each SELEX-identified nucleic acid capture reagent is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method applied to the application of high affinity binding involves selection from a mixture of candidate oligonucleotides and stepwise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, and then reiterating the steps of binding, partitioning, dissociating and amplifying through as many cycles as desired to yield highly specific high affinity nucleic acid ligands to the target molecule. In this manner, aptamers suitable for binding to virtually any target protein can be discovered.

More specifically, SOMAmers are protein-binding aptamers discovered by a modification of the SELEX process to have a rate of dissociation ($t_{1/2}$) generally between and 240 minutes, this being the average time it takes for half of the protein-aptamer complexes to dissociate. In addition, SOMAmers contain modified nucleosides that provide for different built-in functionalities. These functionalities may include tags for immobilization, labels for detection, means to promote or control separation, amino acid-like sidechains to provide better affinity with proteins, and/or the like. The modifications to improve affinity with proteins are commonly chemical groups that are attached to the 5-position of the pyrimidine bases. By functionalizing the 5-position with protein-like moieties (e.g., benzyl, 2-napthyl), the chemical diversity of the SOMAmers is expanded, allowing high affinity binding with a wider range of target molecules. Additionally, some polymerases are still able to transcribe DNA with modifications in these positions, thus allowing the amplification necessary for the SELEX process.

It should be noted that while binding aptamers, including SOMAmers, are commonly discovered by the SELEX process, there may be other means to select them. For example, as computer modeling of molecular interactions improve, it may become possible to directly calculate an ideal nucleic acid sequence for an aptamer and the associated chemical modifications for a SOMAmer to generate capture reagents specific to a given target molecule. Other chemical techniques for screening for aptamers and SOMAmers besides SELEX are also possible.

Assays directed to the detection and quantification of physiologically significant molecules in biological samples and other samples are important tools in scientific research and in the health care field. The SOMAmers are each capable of binding to a target molecule in the sample in a highly specific manner and with very high affinity. After appropriate washing and partitioning steps to first remove unbound proteins and then to remove unbound SOMAmers, the SOMAmers are eluted from the resultant SOMAmer-protein complexes. The SOMAmer eluate is then contacted with a microarray containing complements to the SOMAmers, thereby enabling a determination of the absence, presence, amount, and/or concentration of the target molecules in the sample.

B. Illustrative Hybridization Capture Assay Approach

This section describes a targeted hybridization-capture (HC) assay in which the SOMAmer signals from an assay eluate are replaced by "reporter" DNA molecules containing SOMAmer-specific identification sequences or "SOMA IDs" for sequencing.

Prior to the HC assay described in this section, SOMAmer binding steps have already been performed, resulting in an eluate containing SOMAmer reagents that signify the presence of corresponding target proteins in a sample. For example, and without limitation, the following steps may have been performed to result in a SOMAmer-containing eluate:

(1) Protein-specific SOMAmer reagents labeled with a 5' fluorophore, photocleavable linker, and biotin are immobilized on streptavidin (SA)-coated beads and incubated with one or more samples containing a complex mixture of proteins;

(2) SOMAmer—target protein complexes form on the beads;

(3) The beads are washed, removing the unbound proteins, and the bound proteins are tagged with biotin;

(4) SOMAmer—protein complexes are released from the beads by photocleavage of the linker with UV light;

(5) Incubation in a buffer containing a polyanionic competitor prevents rebinding of dissociated proteins, thereby kinetically enriching for complexes specific to target protein binding with slow off-rates compared to interactions that represent binding of a target protein to a corresponding SOMAmer with fast off-rates;

(6) SOMAmer—protein complexes are recaptured on a second set of streptavidin-coated beads through biotin-tagged proteins, followed by additional washing steps that facilitate further removal of nonspecifically bound SOMAmer reagents; and (7) SOMAmer reagents are released from the beads in a denaturing buffer, forming a SOMAmer-containing eluate suitable for quantitative analysis.

Turning now to the hybridization-capture approach which is the main focus of this section, FIG. 1 schematically depicts a tri-molecular complex, generally indicated at 100, that can be used in a next-generation sequencing assay to identify target proteins. Complex 100 includes a SOMAmer 102, which is a post-assay SOMAmer, i.e., one of the SOMAmers remaining in a SOMAmer-containing eluate after exposure to a biological sample and (for example) the other steps described above. In other words, the presence of SOMAmer 102 in a post-assay eluate signifies the presence of a corresponding target protein (or other target molecule) in the sample.

Complex 100 further includes a first probe 104 and a second probe 106. First probe 104 includes a hybridization region $H_1$ that is complementary to a left-hand portion of SOMAmer 102 in FIG. 1. Second probe 106 includes a hybridization region $H_2$ that is complementary to a right-hand portion of SOMAmer 102 in FIG. 1, and also includes common primer regions $P_1$ and $P_2$, and a unique SOMAmer identification sequence $I_s$ or "SOMA ID" that corresponds to SOMAmer 102 as described in more detail below. $H_1$ and $H_2$ positions may be reversed as well, $H_1$ hybridizing to the right-hand portion of SOMAmer 102 and $H_2$ hybridizing to the left-hand portion of SOMAmer 102 with appropriate reversal of common primer regions $P_1$ and $P_2$, and a unique SOMAmer identification sequence $I_s$ in $H_2$.

Hybridization regions $H_1$ and $H_2$ are configured to specifically bind to the respective complementary portions of the corresponding SOMAmer, and may be designed to have similar melting temperatures ($T_m$) to achieve uniform hybridization under a given set of assay conditions. The hybridization regions of complex 100 may be designed and created, for example, according to the following steps.

First, target regions for the probes are determined on the SOMAmer. For truncated SOMAmers, the full SOMAmer sequence may be used as the target region, including five bases of the fixed region used for amplification in SELEX from each end of the random region. For full-length SOMAmers, the SOMAmer may be truncated to any desired length in silico (i.e., computationally), for example 50-mer, after which the hybridization complements are determined.

Next, a boundary is determined for dividing the target region into two parts. In some examples, to achieve similar melting temperatures for the two hybridization regions, the melting temperatures of the 25-mer (for example) duplex between the SOMAmer and both $H_1$ and $H_2$ may be determined computationally, and then boundary changes between the two regions are stepped through until the melting temperature is maximally balanced between $H_1$- and $H_2$-SOMAmer duplexes. In other examples, different melting temperatures may be intentionally selected, e.g., a first melting temperature (such as 45° C.) for the $H_1$ probes, and a second melting temperature (such as 35° C.) for the $H_2$ probes.

Length constraints may also be imposed on the hybridization regions. For example, a minimum length of 18-mer may be set for both $H_1$ and $H_2$. Similarly, for example, a maximum length of 30-mer may be set for $H_2$, to insure that $H_2$ plus the remaining reporter portions of the second probe remains less than some desired maximum length, such as 100 bases long, for later synthesis. Under these constraints, the hybridization regions $H_1$ and $H_2$ may be generated computationally.

Various factors may be considered when generating the common primer regions $P_1$ and $P_2$ and the SOMAmer ID sequence $I_s$ for the second probes 106. For instance, sequencing amplicon designs for counting applications must find a good balance between the desire for short, cheap reads, and the need for sequences with enough length and information content to serve as identifier sequences like the SOMAmer IDs used for counting and barcode sequences used for multiplexing. For these reasons, when scaling content, the reporter region real estate, which ultimately becomes the largest part of the sequencing template, may be limited in length. For instance, the primer regions $P_1$ and $P_2$ may be limited to 24-mer in length, and the SOMAmer ID sequence $I_s$ may be limited to 15-mer in length, with an edit distance of at least 5 in length and no homopolymer greater than 2-mer in length. Other length constraints and choices are possible for both the primer regions and the SOMAmer ID sequences.

Figure 2A:
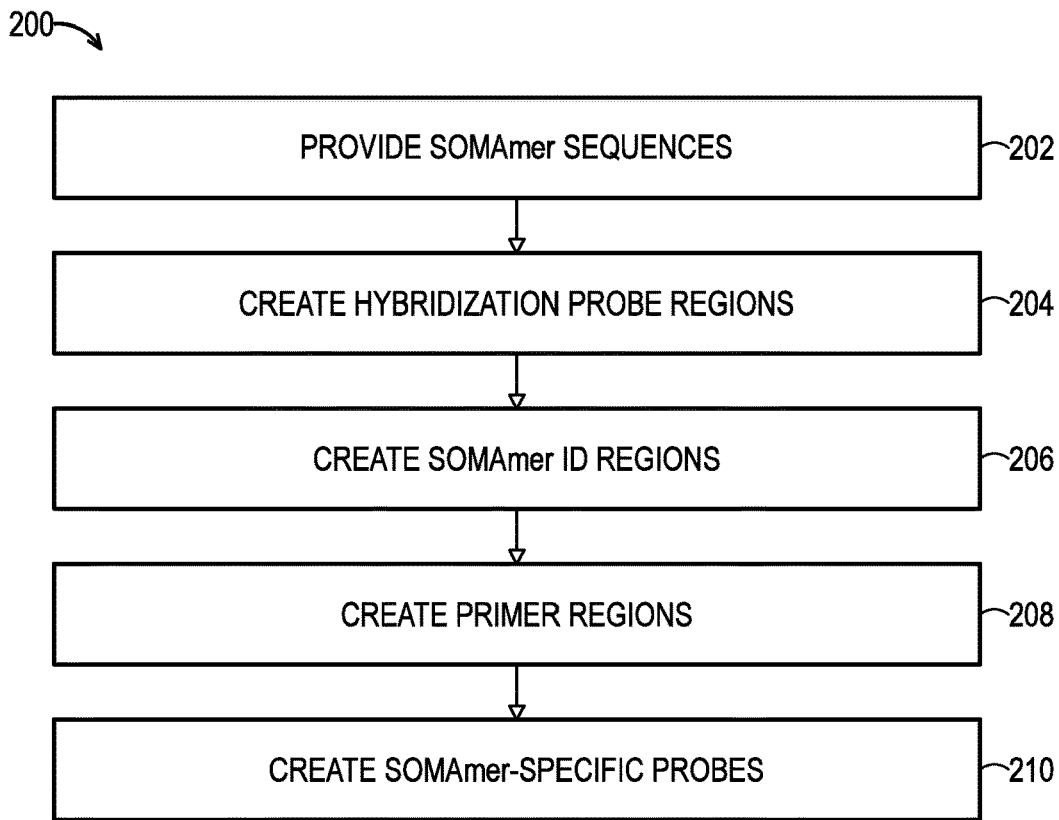
FIG. 2A is a flow chart depicting steps of an illustrative method for creating the hybridization probes required to make the tri-molecular complex of FIG. 1, in accordance with aspects of the present teachings.

FIG. 2A is a flow chart illustrating the steps of an illustrative method 200 for creating the hybridization probes, $H_1$ (104) and $H_2$ (106) used to form the tri-molecular complex of FIG. 1. At step 202, a set of SOMAmer sequences used in the assay is provided.

At step 204, hybridization probe regions $H_1$ and $H_2$ are created. These hybridization probe regions may, for example, be determined computationally under various length and/or other constraints, as described above. Also as described previously, in some cases, the hybridization regions may be partitioned from a single SOMAmer-complementary structure, based on factors such as balancing the melting temperature of each region.

At step 206, SOMAmer ID ($I_s$) regions are created, uniquely corresponding to each SOMAmer. SOMAmer ID regions may be designed by various methods. For instance, the $I_s$ regions may be designed "by eye" (for example, to have maximal edit distances), or they may be generated computationally in conjunction with the computational generation of hybridization regions $H_1$ and $H_2$. After a library of SOMAmer ID regions has been generated, the SOMAmer IDs may be assigned at random or in any other suitable manner to SOMAmers, to create unique reporters corresponding to each SOMAmer.

At step 208, universal primer regions $P_1$ and $P_2$ are created. The universal primers may be designed for stability and to reduce the risk of downstream bias. For example, in some cases the primers may be 24-mers or 25-mers in length, with estimated melting temperatures of −70° C. In some cases, the primers may terminate at the 3' end in a guanine (G) for stability. In some cases, the primers may be assessed with an oligonucleotide (oligo) analyzer to reduce the potential risk of dimer formation. In some cases, the primers may be further tailored to avoid non-specific interactions with the functional oligos employed in known sequencing technologies.

At step 210, first and second SOMAmer-specific probes (sometimes referred to as "capture probes") are created. The first probes each include a hybridization region $H_1$, along with one or more elements suitable for binding to an assay bead, such as biotin for binding to a streptavidin-coated bead. The first probes may also include additional elements such as a photocleavable linker. The second probes each include a hybridization region $H_2$, universal primer regions $P_1$ and $P_2$, and a SOMAmer ID sequence $I_s$. As part of creating the second probes, the SOMAmer ID regions may be appended to the universal primers, to create amplifiable reporters.

Figure 2B:
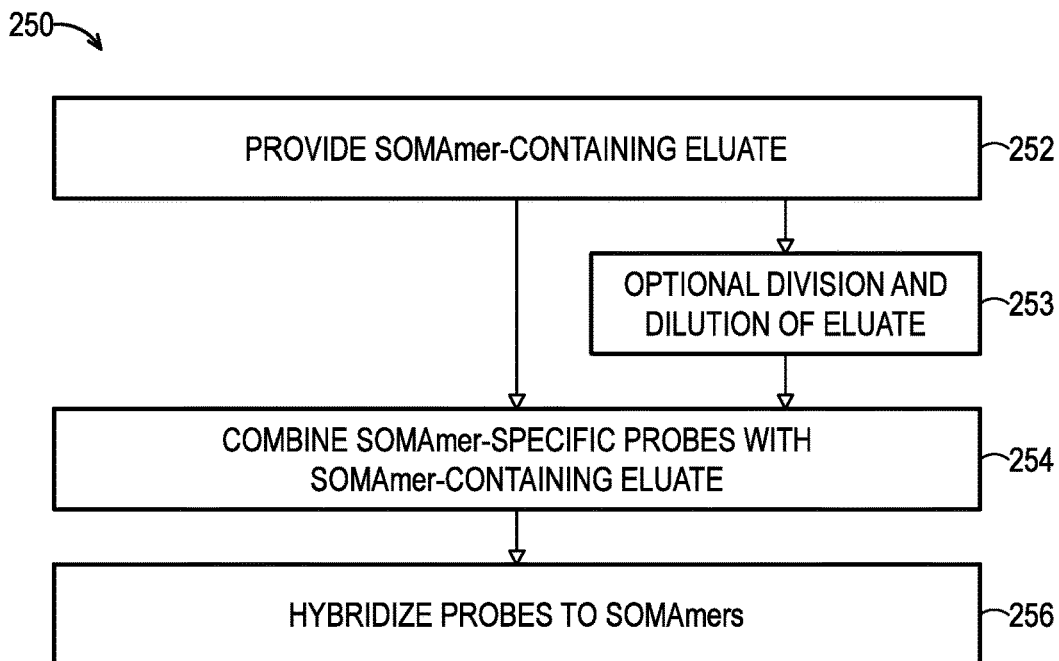
FIG. 2B is a flow chart depicting steps of an illustrative method for creating the tri-molecular complex of FIG. 1, in accordance with aspects of the present teachings.

FIG. 2B is a flow chart illustrating the steps of an illustrative method 250 for creating tri-molecular complexes, such as the tri-molecular complex of FIG. 1. At step 252, a SOMAmer-containing eluate is provided, with SOMAmers in the eluate indicating the presence of one or more target proteins or other target molecules in one or more biological samples that were exposed to a SOMAmer library, as described previously.

At step 254, a set or library of the SOMAmer-specific capture probes created by method 200 are combined with a post-assay, SOMAmer-containing eluate. In one example, 25 µl of SOMAmer-containing eluate is combined with 25 µl of probe-containing solution, resulting in a 50 µl hybridization volume. To promote hybridization, the capture probes may have a concentration comparable or greater than the concentration of SOMAmers in the eluate. For example, a suitable concentration of probes may fall in the range of 0.05 nM-5.0 nM, such as 0.5 nM (where nM=nanomoles per liter).

In some cases, in an optional step 253 of method 250, SOMAmer-containing eluate may be divided and selectively diluted before hybridization, and then recombined before sequencing. More specifically, the post-assay eluate may be divided into two or more dilution groups (for instance, four dilution groups), based on the expected relative abundance of SOMAmers in each group. The least concentrated (most diluted) sample may contain the most abundant SOMAmers in the eluate. Conversely, the most concentrated (least diluted) sample may contain the least abundant SOMAmers in the eluate. In this manner, SOMAmer counts may be "leveled" to improve accuracy and precision in the detection of less abundant SOMAmers. Each dilution group may then be hybridized separately through exposure to a corresponding subset of probes. Further details about the use of dilution groups will be provided in a subsequent section of this disclosure.

Additionally, leveling may be accomplished by introducing a fixed ratio of $H_1$ probes with and without a capture tag for certain high abundant SOMAmers in the eluate. SOMAmers that form tri-molecular complexes with $H_1$ probes lacking a capture tag will be removed during wash steps as detailed below in method 300.

At step 256, the first and second probes are hybridized to the SOMAmers, forming tri-molecular complexes that each include (i) a SOMAmer, (ii) a first probe bound to the SOMAmer through hybridization region $H_1$, and (iii) a second probe bound to the SOMAmer through hybridization region $H_2$. The second probes each include a SOMAmer ID sequence $I_s$, which can be sequenced to signify the presence of a corresponding SOMAmer in the eluate, and therefore to signify the presence of a corresponding protein captured by that SOMAmer in the original biological sample. Hybridization of the capture probes to the SOMAmers can be accomplished using any suitable technique, such as appropriate thermocycling and may include additives to enhance hybridization kinetics.

Figure 3A:
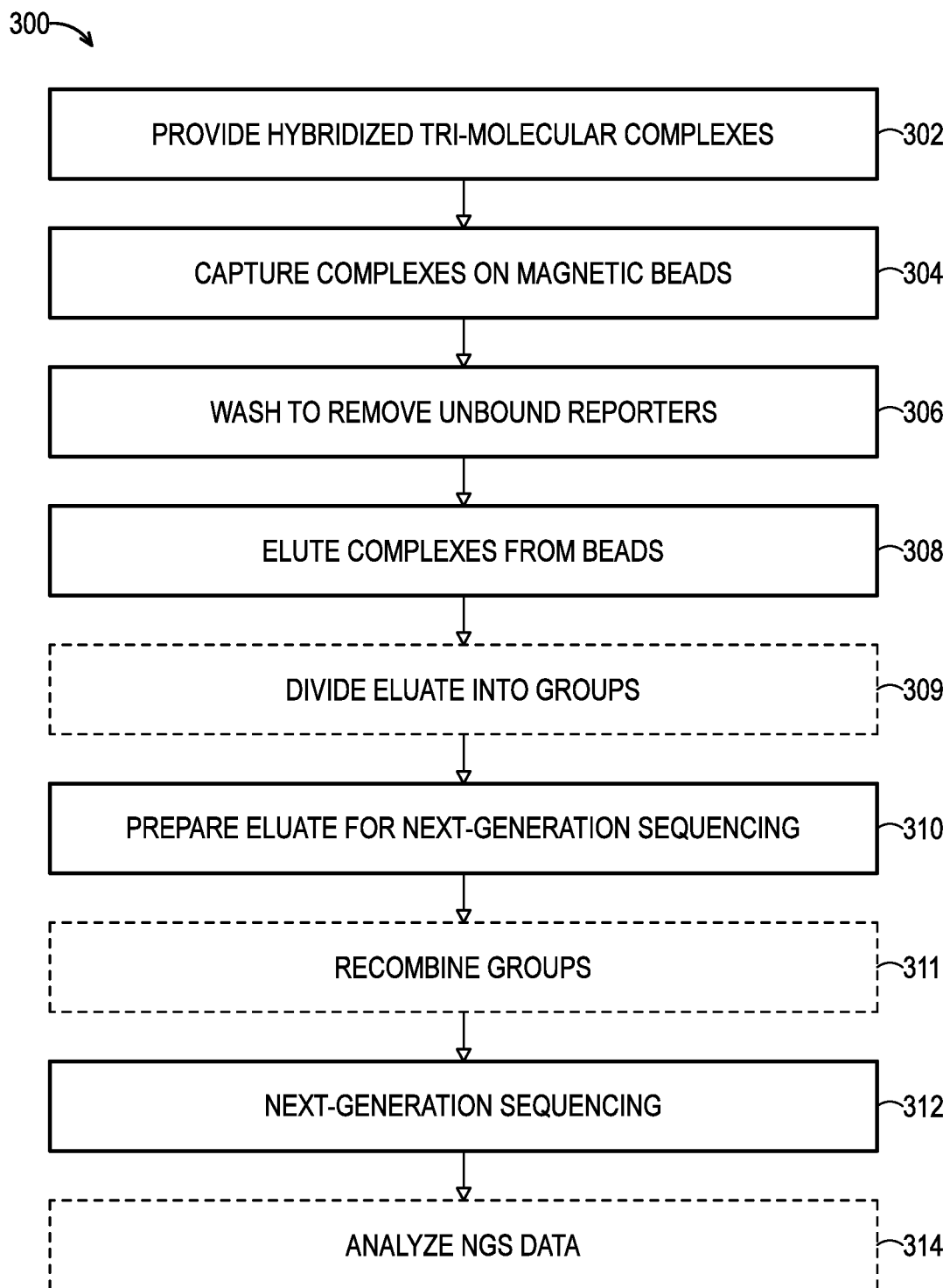
FIG. 3A is a flow chart depicting steps of an illustrative method for performing a next-generation sequencing assay using tri-molecular complexes such as the complex depicted in FIG. 1, in accordance with aspects of the present teachings.

FIG. 3A is a flow chart illustrating the steps of an illustrative method 300 for performing a next-generation sequencing assay using the tri-molecular complexes such as those depicted in FIG. 1, and created by a method such as the method of FIG. 2B. At step 302, hybridized tri-molecular complexes corresponding to a desired library of post-assay SOMAmers (e.g., each having a structure such as the structure of complex 100, and created according to a method such as method 250) are provided for a sequencing assay.

At step 304, the tri-molecular complexes are captured on magnetic beads. For example, the complexes may be captured through binding of biotin attached to the hybridization regions $H_1$ of the first probes with streptavidin on the beads. Capture may be accomplished through any suitable technique. For instance, in one example, the hybridization volume may be combined with 30 µl of solution containing beads at a concentration of 20 mg/ml, followed by mixing with a thermomixer for 30 minutes at 1200 rpm at a temperature of 45° C.

At step 306, the solution containing bead-captured probes is washed one or more times to remove unbound $H_2$ probe-reporters, i.e., probes that were not hybridized to a corresponding SOMAmer. For instance, washing may be performed with a suitable buffer solution such as a 20 mM phosphate buffer solution with 1 mM EDTA and 0.05% SDS (sodium dodecyl sulphate). Washing phases may be performed statically, dynamically using a thermomixer, or a sequential combination of both types. In one example, there may be two static 5-minute washing phases and two 10-minute dynamic washing phases at 1200 rpm. In any event, after washing, the resulting solution should contain tri-molecular complexes bound to beads, with at most a small remaining amount of unbound $H_2$ probes/reporters.

In certain embodiments of SOMAmer eluate leveling, or dynamic range compression, the tri-molecular complexes lacking a bead capture tag on $H_1$ will be removed as well as unbound $H_2$ probe-reporters at step 306. These complexes will reduce the copies of those SOMAmers in the final NGS sequencing, thereby lowering the counts on these abundant SOMAmers.

At step 308, the bound tri-molecular complexes are eluted from the beads to which they are attached, for example by exposure to a solvent, heat, or by any other suitable elution method. The components of the complexes also may be dissociated as part of this step, resulting in separated SOMAmers and probes. In one example, complexes are eluted by adding 85 µl of NaOH at concentration 20 mM to the eluate containing the bound complexes, followed by mixing for three minutes at 1200 rpm with a thermomixer and five minutes for partitioning of the complexes. The solution containing eluted complexes may then be combined with 20 µl of HCL.

In some examples, the eluted solution (i.e., the eluate) resulting from step 308 may be divided and/or diluted into two or more groups, such as four dilution groups or primer amplification groups, in an optional step 309 of method 300. As described previously in the context of method 250, using multiple dilution groups or primer amplification groups (which in some cases may not be diluted) corresponding to subsets of SOMAmers having different expected abundances serves to level the relative abundances, or compress the large range of distribution, of the overall set of SOMAmers, to allow greater accuracy and precision in detecting relatively scarce target molecules. Dividing into such groups can be done before hybridization (as in step 253 of method 20), after hybridization as in the presently described step 309, or both. Further details of possible dilution and recombination techniques will be described in a subsequent section of this disclosure.

At step 310, the solution(s) resulting from step 308 and optional step 309 are prepared for next-generation sequencing (NGS). This may include PCR amplification of the reporter regions containing the common primers ($P_1$ and $P_2$ in FIG. 1) along with the associated SOMAmer ID sequences $I_s$. Preparation for NGS also may include attaching adapter sequences and/or barcode sequences for demultiplexing, if eluates from multiple samples are to be combined prior to sequencing. The creation and attachment of adaptor and barcode sequences to reporter regions can be accomplished in any suitable manner known in the art, as has become commonplace when preparing samples for next-generation sequencing. In some cases, barcode sequences may be added as part of a first preparation step, and NGS adaptors may be added as part of a second preparation step.

At an optional step 311, any groups that remain separated after step 310 may be recombined in preparation for sequencing.

At step 312, the prepared sample(s) are sequenced using next-generation sequencing techniques. In some examples, the prepared samples may be sequenced using a next-generation sequencing platform developed by Illumina, Inc. of San Diego, California. However, the presently disclosed methods are also suitable for use with other NGS sequencing platforms.

After NGS, the data obtained through sequencing may be analyzed or otherwise processed in an optional step 314, to determine the concentrations of analytes, such as target proteins, in the original biological samples. Generally speaking, this analysis involves demultiplexing the sequencing data using the barcodes corresponding to each original sample (if multiple samples were multiplexed), counting reporter sequences, and scaling and/or normalizing the data to extract accurate results. For purposes of analysis, the sequencing data may be written to a data file in a standard format, such as the ADAT format developed by SomaLogic. Possible quantitative analysis methods are discussed in more detail below.

Figure 3B:
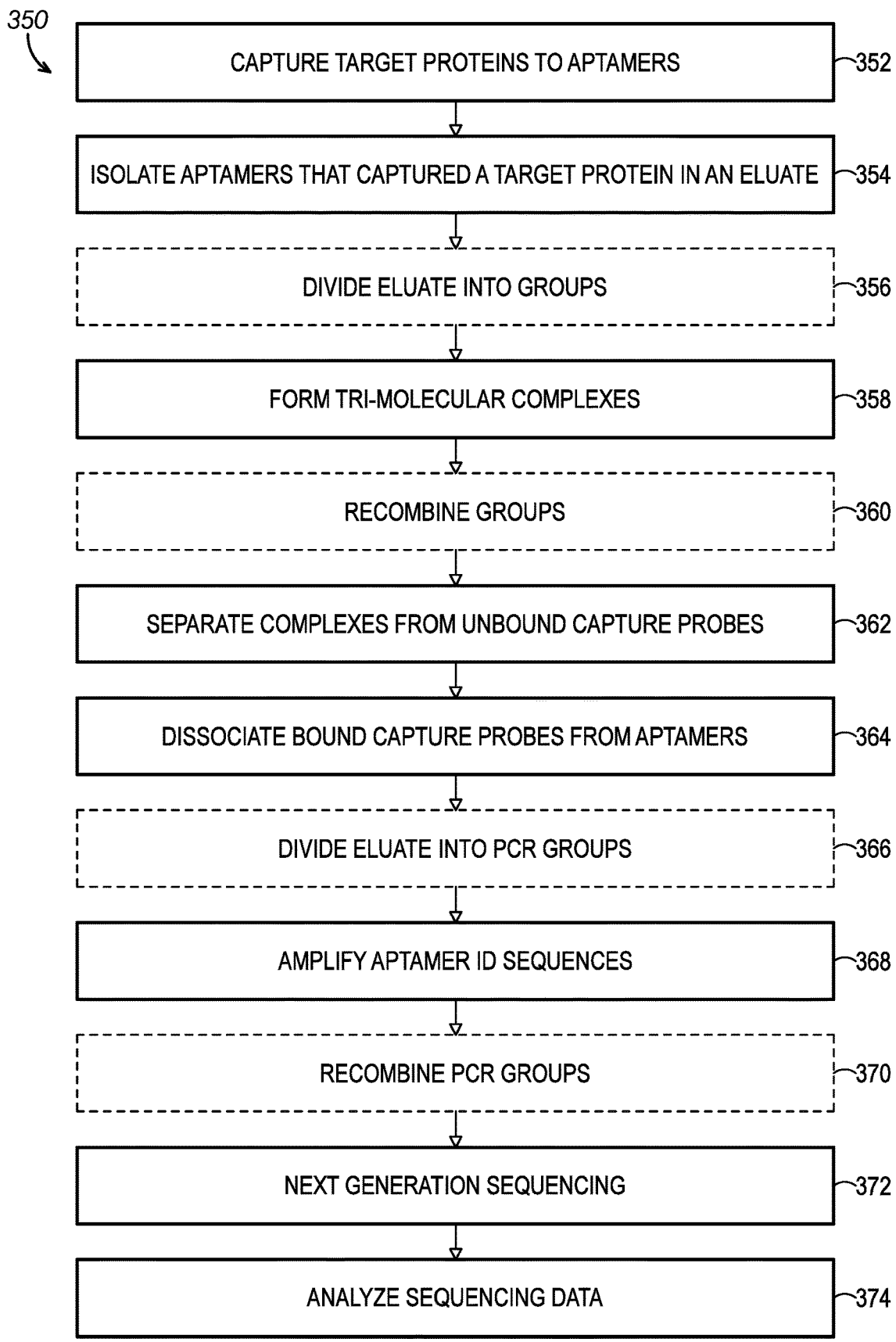
FIG. 3B is a flow chart depicting steps of an illustrative method for performing a next-generation sequencing assay that includes capturing target proteins and then forming tri-molecular complexes such as the complex depicted in FIG. 1, in accordance with aspects of the present teachings.

FIG. 3B is a flow chart illustrating the steps of an illustrative method 350 for performing a next-generation sequencing assay that includes capturing target proteins with aptamers, forming tri-molecular complexes from the aptamers, and then using the tri-molecular complexes as the basis for identifying the captured target proteins. It should be understood that any of the steps of method 350 may be similar to corresponding steps of methods described previously (i.e., methods 200 and 300), and therefore may not be described again in the same detail.

At step 352 of method 350, target proteins are captured by exposing a biological sample to a plurality of aptamers, such as SOMAmers, each configured to bind to a specific protein. By exposing the sample to a library of many such SOMAmers, a large number of target protein species may be detected in a single assay.

At step 354, the aptamers that captured one of the target proteins are isolated in an aptamer-containing eluate. Forming an aptamer-containing eluate may be accomplished, for example, in a so-called SomaScan Assay process performed by SomaLogic, which includes binding the aptamers to assay beads, capturing proteins with the aptamers, washing away unbound proteins, tagging the bound proteins with biotin, releasing the aptamers from the beads, capturing the tagged proteins to new beads, removing unbound aptamers, denaturing the aptamers from the captured proteins, and then separating the aptamers into an eluate.

At optional step 356, the aptamer-containing eluate may be split into a plurality of groups, which may be dilution groups, as will be described in more detail below with respect to FIGS. 4-6 and FIG. 11.

At step 358, a plurality of tri-molecular complexes are formed by exposing the aptamers in the eluate (or each eluate dilution group) to a plurality of capture probes each configured to hybridize to a particular aptamer. For example, each complex may have a structure similar to the structure of complex 100 depicted in FIG. 1. Accordingly, each tri-molecular complex includes (i) a particular one of the aptamers from the eluate; (ii) a first capture probe including a portion hybridized to a first portion of the aptamer; and (iii) a second capture probe including a portion hybridized to a second portion of the aptamer, and further including one or more DNA primer regions and an aptamer ID sequence corresponding to the particular aptamer. If separate dilution groups were formed, each dilution group will be exposed to a different set of capture probes corresponding to a different subset of aptamers. Optionally, some of the $H_1$ probes may lack bead capture tags for additional leveling of SOMAmer counts.

At step 360, groups formed in step 356 (if any) may be recombined.

At step 362, the tri-molecular complexes are separated from capture probes not bound to aptamers. For instance, the hybridized complexes may be captured to magnetic beads, following by washing to remove the unbound probes.

At step 364, the capture probes in the tri-molecular complexes are dissociated from the corresponding aptamers. This may include eluting the complexes from the beads, but in any case the result of step 362 is that the capture probes are no longer bound to the aptamers.

At step 366, the eluate containing unbound capture probes may optionally be divided and/or diluted (potentially for a second time, as discussed below with respect to FIG. 6) to form a plurality of PCR groups.

At step 368, the aptamer ID sequences in the dissociated capture probes of the eluate are amplified, for instance through PCR amplification of the DNA primer region(s) and the associated ID sequences. Additional preparation for NGS may also be performed at this stage, such as attaching adapter sequences and/or demultiplexing barcode sequences.

At step 370, separated PCR groups (if any) may be recombined.

At step 372, the aptamer ID sequences are sequenced using next-generation sequencing techniques. In some examples, this may be accomplished using a next-generation sequencing platform developed by Illumina, Inc. of San Diego, California.

At step 374, the data obtained by sequencing the aptamer ID sequences may be used to determine the abundances of target proteins in the original biological samples.

C. Exemplary Dilution Groups or Dynamic Range Compression for Next-generation Sequencing This section describes possible methods of diluting assay eluates to achieve greater assay efficiency, reproducibility, performance, and/or production feasibility in next-generation sequencing systems, according to aspects of the present teachings; see FIGS. 4-6.

First, it should be understood that it is possible to perform NGS on a SOMAmer-containing eluate without dividing the eluate into dilution groups, i.e., in a single eluate solution that has never been divided, diluted, or recombined. Such an assay is within the scope of the present teachings, and has the advantages that less eluate is required, and only one hybridization plate is needed for every 96 samples. However, such an assay has sensitivity and precision challenges, for example due to the possibility of an extreme range of SOMAmer abundances in the original eluate, potentially spanning several orders of magnitude. For example, target proteins in a sample could have concentrations in the range of fM-μM (i.e., spanning around nine orders of magnitude), resulting in eluate SOMAmer concentrations that span five or more orders of magnitude. Performing an assay on such an eluate may lead to overcounting of more abundant SOMAmers and corresponding undercounting of less abundant SOMAmers. Accordingly, it may be desirable to level, or compress the range of abundances of SOMAmers before sequencing and counting.

Systems and methods of the present disclosure address this problem by subdividing the SOMAmers into subpopulations before counting, which, in combination with dilutions, results in leveling, or dynamic range compression, of the counts across the subpopulations upon combining them back together for sequencing and counting. In some examples, the set of SOMAmer probes are sub-divided into sub-populations based on SOMAmer eluate abundance (rare SOMAmers in a first group, semi-rare SOMAmers in a second group, abundant SOMAmers in a third group, etc.). The dynamic range in each sub-population is smaller, and in some examples much smaller, than the dynamic range of the original (undivided) eluate. As described below, dilution groups may be formed before and/or after hybridization of the SOMAmers to probes, i.e., before and/or after the formation of tri-molecular complexes suitable for NGS.

In addition to leveling by dilution, high abundant SOMAmers may be 'leveled' by introducing $H_1$ probes that lack bead capture tags along with those probes containing the tags. The ratio of $H_1$ probes with and without bead capture tags will reduce the tri-molecular complexes captured in step 304 of method 300 and step 358 of method 350 by an amount corresponding to the ratio. For example, if the ratio of untagged to tagged probes is 10:1, only ten percent of the tri-molecular complexes will be captured, lowering the counts in the NGS output by an order of magnitude compared to an assay without untagged probes. The ratio of untagged to tagged probes may be different for different SOMAmers, depending on the expected count for each SOMAmer.

1. Four Hybridization Groups

Figure 4:
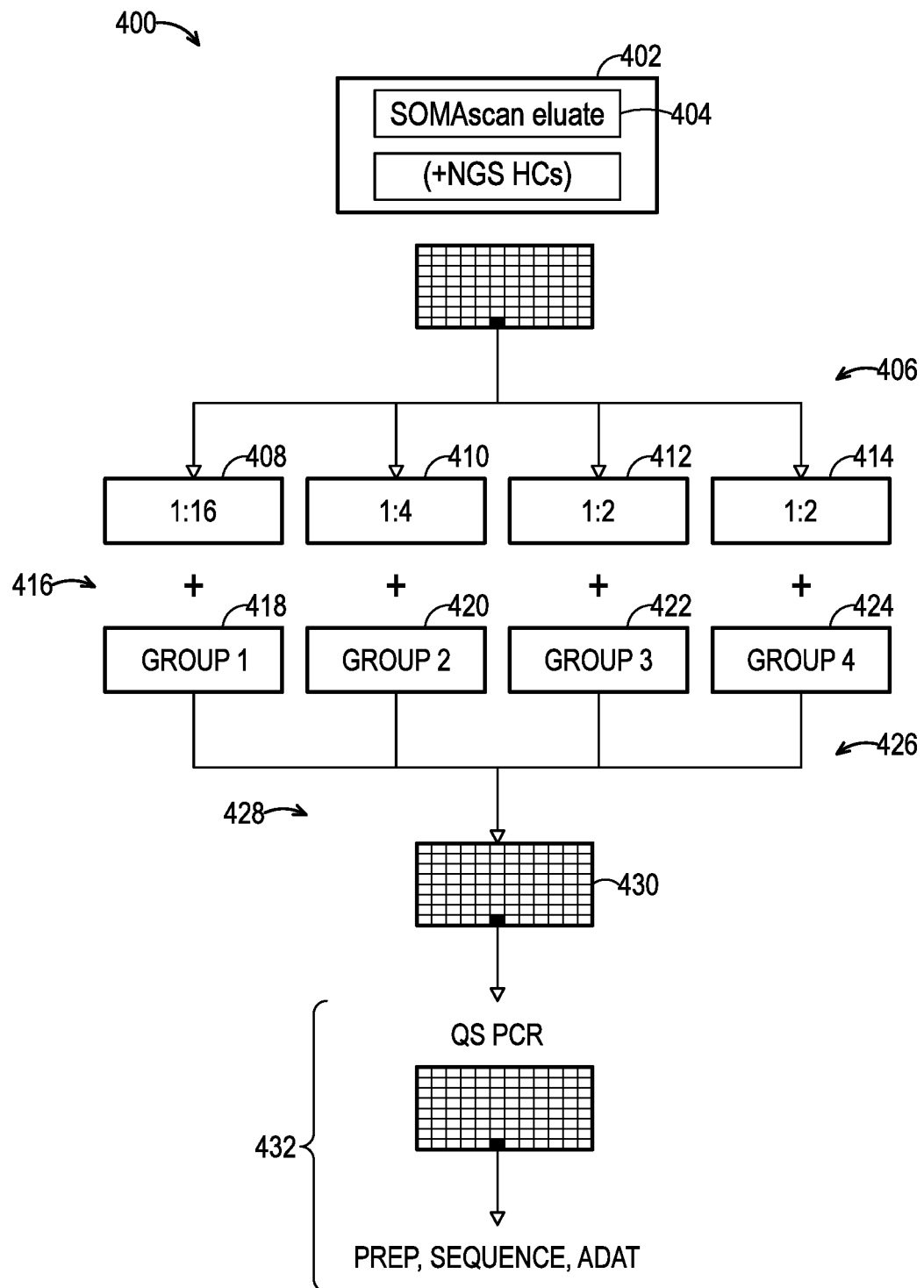
FIG. 4 is a flow diagram depicting the steps and byproducts of an exemplary next-generation sequencing assay involving four hybridization groups, in accordance with aspects of the present teachings.

FIG. 4 depicts the steps and byproducts of an exemplary NGS assay, generally indicated at 400, which involves four hybridization groups. At step 402, a SOMAmer-containing eluate 404 is provided. Eluate 404 contains SOMAmers resulting from prior exposure to a biological sample and separation from target molecules, as has been described previously.

At step 406, eluate 404 is divided into four equal parts or aliquots 408, 410, 412, and 414. In the assay of FIG. 4, aliquot 408 is diluted by a ratio of 1:16, i.e., one part eluate to 16 parts buffer solution; aliquot 410 is diluted by a ratio of 1:4; and aliquots 412 and 414 are each diluted by a ratio of 1:2. In some cases, the aliquots may not be diluted.

At step 416, the four aliquots are each combined with a group of hybridization capture probes 418, 420, 422, and 424, respectively labeled "Group1," "Group2," "Group3," and "Group4." In this example, capture probe group 418 is combined with the most diluted eluate, and therefore contains capture probes configured to bind with the most common SOMAmers in the eluate. Similarly, capture probe group 420 contains probes configured to bind with the next most common SOMAmers, and capture probe groups 422 and 424 each contain probes configured to combine with different subsets of relative less abundant SOMAmers. Thus, the result of step 416 is four separate solutions, each configured to result, upon hybridization, in a set of tri-molecular compounds each including a SOMAmer and corresponding probes hybridized to the SOMAmer. Each compound may be generally similar to compound 100 of FIG. 1.

Any of the four groups of hybridization capture probes may contain fixed ratios of $H_1$ probes with and without a bead capture tag for some subset of SOMAmers within each group for additional leveling of counts.

At step 426, the four solutions generated by step 416 are each hybridized, captured to beads, washed, and eluted. This may be accomplished, for example, as described previously with respect to steps 304, 306, and 308 of method 300 depicted in FIG. 3A.

At step 428, the separate eluates resulting from step 426 are recombined into a single eluate solution 430. In some cases, the separate solutions may be recombined at different volumes, resulting in further dilution of relatively abundant capture groups (i.e., corresponding to abundant SOMAmers and thus to abundant species of target molecules in the original biological sample). This results in a normalized combined solution with less overall variation in the concentrations of different tri-molecular compounds, which may be analyzed with relatively fewer sequencing "reads." For example, the combination of dilution and normalization might reduce the number of required reads per sample from around 200 million to fewer than five million, allowing multiplexing of many samples per sequencing run and reducing the cost per sample while still achieving an acceptable precision as measured by the coefficient of variation (CV) in the results.

At step 432, which may be viewed as the combination of previously described steps 310, 312, and 314 of method 300, solution 430 resulting from step 428 is prepared for next-generation sequencing (NGS), sequenced, and the results are written to a data file and analyzed as desired. Preparation may include PCR amplification of the reporter regions containing the common primers ($P_1$ and $P_2$ in FIG. 1) along with the associated SOMAmer ID sequences $I_s$. As discussed previously, preparation also may include attaching adapter sequences and/or barcode sequences for demultiplexing to the tri-molecular compounds. The prepared solution is then sequenced using NGS techniques, such as using a next-generation sequencing platform developed by Illumina, Inc. of San Diego, California, or any other NGS sequencing platform. After NGS, the data obtained through sequencing may be analyzed or otherwise processed to determine the concentrations of analytes, such as target proteins, in the original biological samples. This may include demultiplexing the sequencing data using the barcodes corresponding to each original sample (if multiple samples were combined), counting reporter sequences, and scaling and/or normalizing the data to extract accurate results. The sequencing data may be written to a data file in a standard format, such as the ADAT format developed by SomaLogic.

2. Single Hybridization Group with Four PCR Groups

Figure 5:
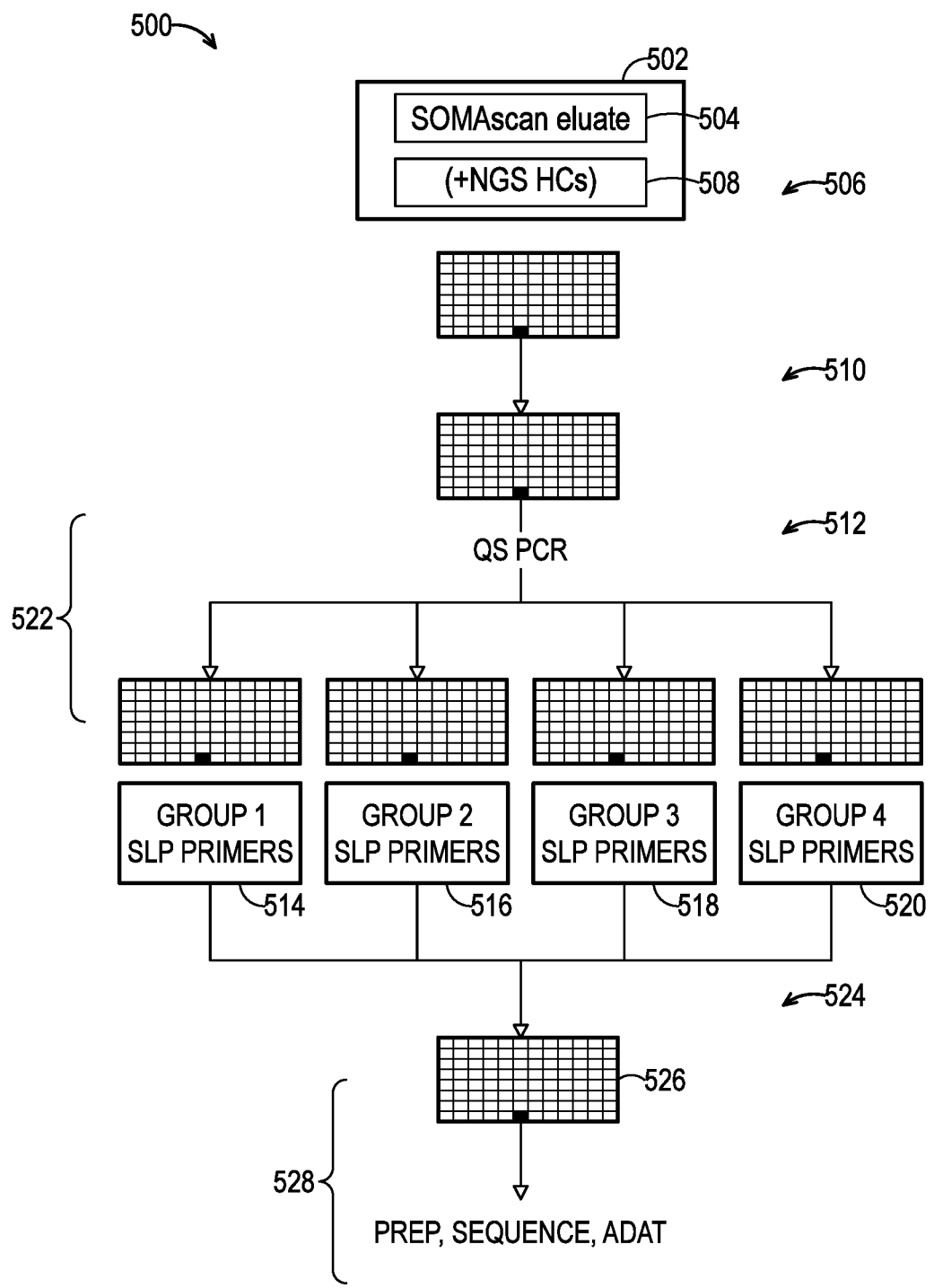
FIG. 5 is a flow diagram depicting the steps and byproducts of an exemplary next-generation sequencing assay involving a single hybridization group and four PCR groups, in accordance with aspects of the present teachings.

FIG. 5 depicts the steps and byproducts of an exemplary NGS assay, generally indicated at 500, which involves a single hybridization group and four PCR groups. At step 502, a SOMAmer-containing eluate 504 is provided. Eluate 504 contains SOMAmers resulting from prior exposure to a biological sample and separation from target molecules, as has been described previously.

At step 506, eluate 504 is combined with a complete set of hybridization capture probes 508, i.e., a set of probes configured to combine with all of the SOMAmers in the eluate. The set of probes may also contain a fixed ratio of tagged and untagged $H_1$ probes as described above.

At step 510, the solution resulting from step 506 is hybridized, captured to beads, washed, and eluted. This may be accomplished as described with respect to steps 304, 306, and 308 of method 300 depicted in FIG. 3A. In this case, however, four sets of universal primers may be used rather than just one, with each set of primers associated with a different set of SOMAmer IDs, corresponding to a set of SOMAmers falling into a particular expected range of concentrations. In other words, step 510 results in four distinct groups of tri-molecular compounds corresponding to different abundancy groups of SOMAmers and therefore to different abundancy groups of target molecules in the SOMAmer eluate from the original biological sample, each of which includes different PCR primers and can therefore be amplified separately.

At step 512, the eluate resulting from step 510 is divided into four equal parts or aliquots 514, 516, 518, and 520. Each aliquot may optionally be diluted to any desired degree at this stage, to normalize the expected concentration of SOMAmer ID sequences to be amplified in the next step. However, FIG. 5 does not depict any dilution in step 512.

At step 522, the separate eluates resulting from step 512 are prepared for next-generation sequencing (NGS), including PCR amplification of the reporter regions. In this case, however, different sets of primers and associated reporter regions are amplified in each separate eluate, resulting of amplification of just a known subset of SOMAmer ID sequences in each eluate.

At step 524, the separate solutions containing amplified SOMAmer ID sequences in each aliquot are recombined into a single eluate solution 526. In some cases, the separate solutions may be recombined at different volumes, resulting in a desired degree of dilution of relatively abundant SOMAmer ID sequences, and a normalized combined solution with less overall variation in SOMAmer ID concentrations, which may be analyzed with relatively fewer reads.

At step 528, solution 526 is further prepared for next-generation sequencing (NGS), sequenced, and the results are written to a data file and analyzed as desired. Preparation of the amplified eluates may include attaching adapter sequences and/or barcode sequences for demultiplexing to the reporter regions of the tri-molecular compounds. The prepared solution is then sequenced using NGS techniques, after which the data obtained from sequencing may be analyzed or otherwise processed to determine the concentrations of target analytes in the original biological samples, as described previously.

3. Four Hybridization Groups and Four PCR Groups

Figure 6:
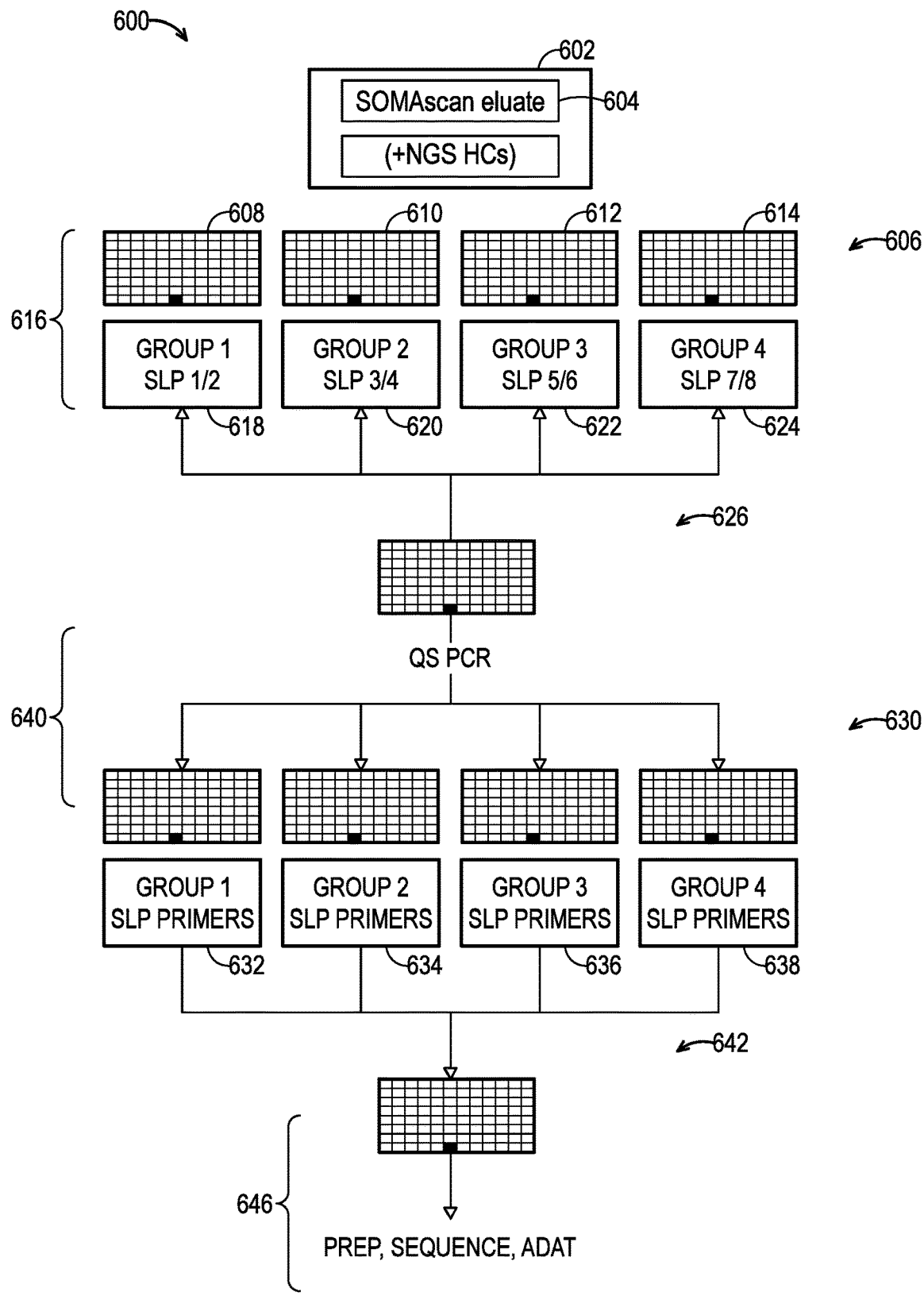
FIG. 6 is a flow diagram depicting the steps and byproducts of an exemplary next-generation sequencing assay involving four hybridization groups and four PCR groups, in accordance with aspects of the present teachings.

FIG. 6 depicts the steps and byproducts of an exemplary NGS assay, generally indicated at 600, which involves four hybridization groups and four PCR groups, and therefore combines aspects of assays 400 and 500 of FIGS. 4-5. At step 602, a SOMAmer-containing eluate 604 is provided, containing SOMAmers resulting from prior exposure to a biological sample and separation from target molecules.

At step 606, eluate 604 is divided into four equal parts or aliquots 608, 610, 612, and 614. These aliquots may optionally be diluted to varying degrees, or in some cases, the aliquots may not be diluted.

At step 616, the four aliquots are each combined with a group of hybridization capture probes 618, 620, 622, and 624, respectively labeled "Group1," "Group2," "Group3," and "Group4," each of which is configured to bind with a different subset of SOMAmers in the eluate, and then the aliquots are separately hybridized. Thus, the result of step 616 is four separate solutions, each containing a set of tri-molecular compounds including a SOMAmer and corresponding probes hybridized to the SOMAmer. Each compound may be generally similar to compound 100 of FIG. 1.

Each of the four hybridization capture probe groups may optionally contain a fixed ratio of untagged and tagged $H_1$ probes for further leveling of counts.

At step 626, the four hybridized solutions generated by step 616 are combined into a single eluate 628, and then sequentially captured to beads, washed, and eluted. This may be accomplished, for example, as described previously with respect to steps 304, 306, and 308 of method 300 depicted in FIG. 3A. As described previously, each hybridized solution may or may not be diluted prior to recombination, and differential volume of each group also may be used to compress analyte variation prior to bead capture and washing.

At step 630, the eluate resulting from step 626 is divided into four equal parts or aliquots 632, 634, 636, and 638. Each aliquot may optionally be diluted to any desired degree at this stage, to normalize the expected concentration of SOMAmer ID sequences to be amplified in the next step. However, FIG. 6 does not depict any dilution in step 630.

At step 640, the separate eluates resulting from step 630 are prepared for next-generation sequencing (NGS), including PCR amplification of the reporter regions. As in assay 500 of FIG. 5, different sets of primers and associated reporter regions are amplified in each separate eluate, resulting of amplification of a subset of SOMAmer ID sequences in each eluate.

At step 642, the separate solutions containing amplified SOMAmer ID sequences in each aliquot are recombined into a single eluate solution 644. In some cases, the separate solutions may be recombined at different volumes, resulting in a desired degree of dilution of relatively abundant SOMAmer ID sequences, and a normalized combined solution with less overall variation in SOMAmer ID concentrations, which may be analyzed with relatively fewer reads.

At step 646, solution 644 is further prepared for NGS, sequenced, and the results are written to a data file and analyzed as desired. Preparation of the amplified eluates may include attaching adapter sequences and/or barcode sequences for demultiplexing to the reporter regions of the tri-molecular compounds. The prepared solution is then sequenced using NGS techniques, after which the data obtained from sequencing may be analyzed or otherwise processed to determine the concentrations of target analytes in the original biological samples.

D. Quantitative Spike Normalization of PCR Groups

In an NGS-based system, signals are measured as sequence read counts, with the read counts for all analytes of a given sample measured in the same sequencing mix with a fixed or finite set of total reads. As proportions of the same mixture, the NGS read counts of all the analytes measured in a given sample affect each other, such that the signal counts observed per analyte are the "net result" of increases and decreases of all the analytes measured in a "zero sum game" per sample with fixed total reads. More specifically, in an NGS system with a fixed number of total reads, any increase in one analyte count results in a corresponding decrease in the other analyte counts, with the decrease distributed according to each analyte's fraction of the total reads.

Figure 7:
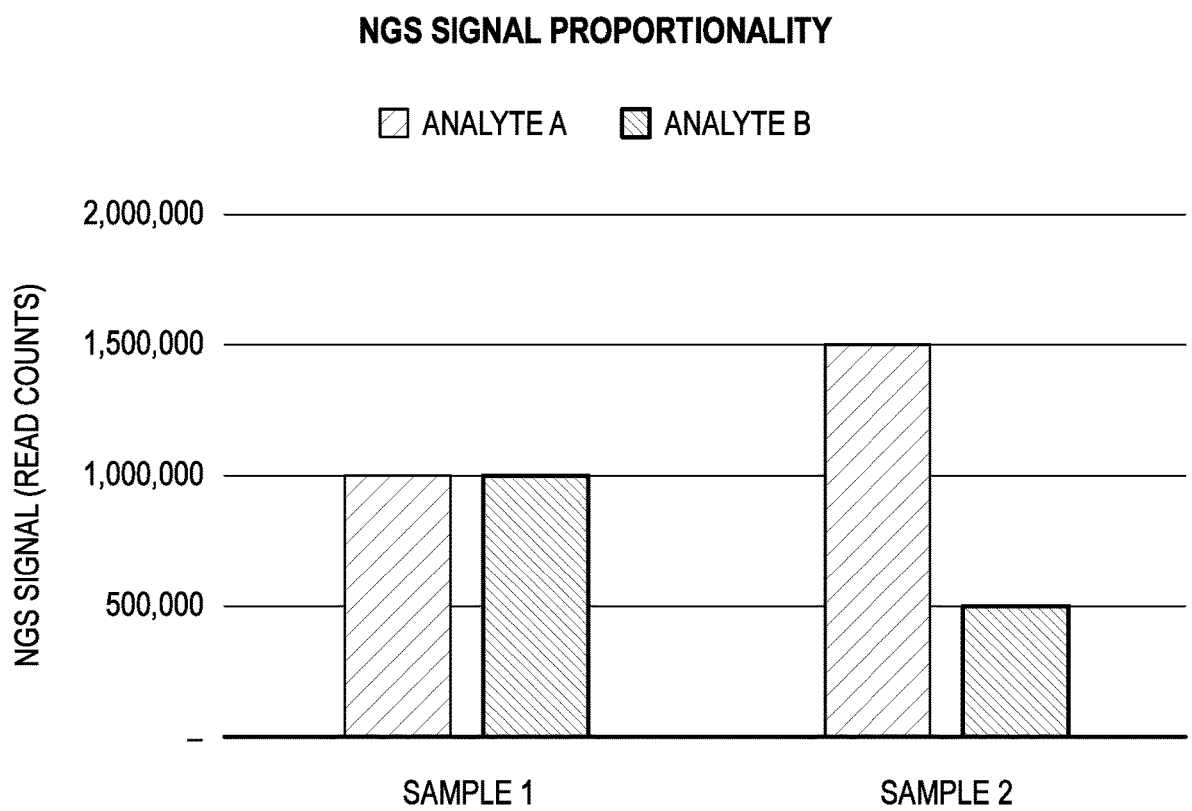
FIG. 7 is a graph depicting in histogram form the results of a hypothetical, simplified two-analyte assay of two separate samples.

FIG. 7 depicts this "zero sum game" graphically, by depicting the results of a simplified two-analyte assay of two separate samples in the form of a histogram, where the vertical axis represents the total number of read counts for each analyte, and the total number of read counts is fixed at two million. In Sample 1, analytes A and B have equal counts. In Sample 2, it appears that analyte A has increased by a half million counts, and analyte B has decreased proportionally by a half million counts. However, because of the finite number of total reads, it is impossible to know from FIG. 7 if the count difference between analytes A and B in sample 2 is due to an increase in analyte A, a decrease in analyte B, or a combination of both.

Figure 8:
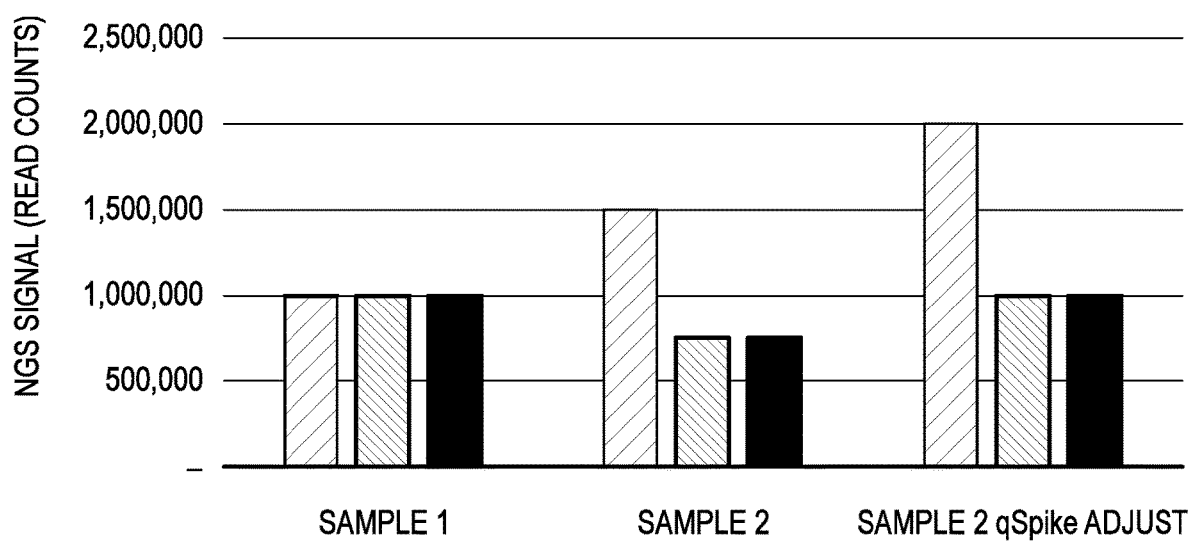
FIG. 8 is a graph depicting the results of the assay of FIG. 7 with the addition of a quantitative spike (qSpike) control reporter added to both samples at the same concentration, in accordance with aspects of the present teachings.

FIG. 8 depicts how the introduction of a reference reporter, or quantitative spike control reporter ("qSpike"), can be used to normalize compensatory read counts across samples, allowing true signal changes to be discerned. In the NGS assay represented in FIG. 8, a qSpike reporter has been physically added (spiked) into the two-analyte system containing analytes A and B, at the same known concentration across all samples. In this case, the qSpike reporter happens to be the same concentration as analytes A and B in Sample 1. In Sample 2, as before, an increase in analyte A and decrease in Analyte B is observed. However, now a decrease in the qSpike can be observed in Sample 2 relative to Sample 1, which we know had the same concentrations of qSpike added. Scaling/adjusting all analytes in Sample 2 to push the spike back to its expected concentration permits the increase in Analyte A relative to Analyte B to be clearly discerned, as indicated by the "Sample 2 qSpike Adjust" histogram in FIG. 8.

In a more realistic NGS assay, a mixture of several qSpike reference reporters may be used to correct compensatory changes in analyte counting proportionality. For instance, an assay according to the present teachings may use a mixture of four unique $H_2$ reporters, i.e., four unique amplifiable reporters forming portions of second probes that are introduced after elution of tri-molecular complexes in step 308 of assay 300 depicted in FIG. 3A, for example. Alternatively, particular qSpike SOMAmers may be introduced into the eluate and the appropriate qSpike reporters are contained in the library of SOMAmer-specific probes. The qSpike reporters or SOMAmers may be provided at different relative concentrations.

Figure 9:
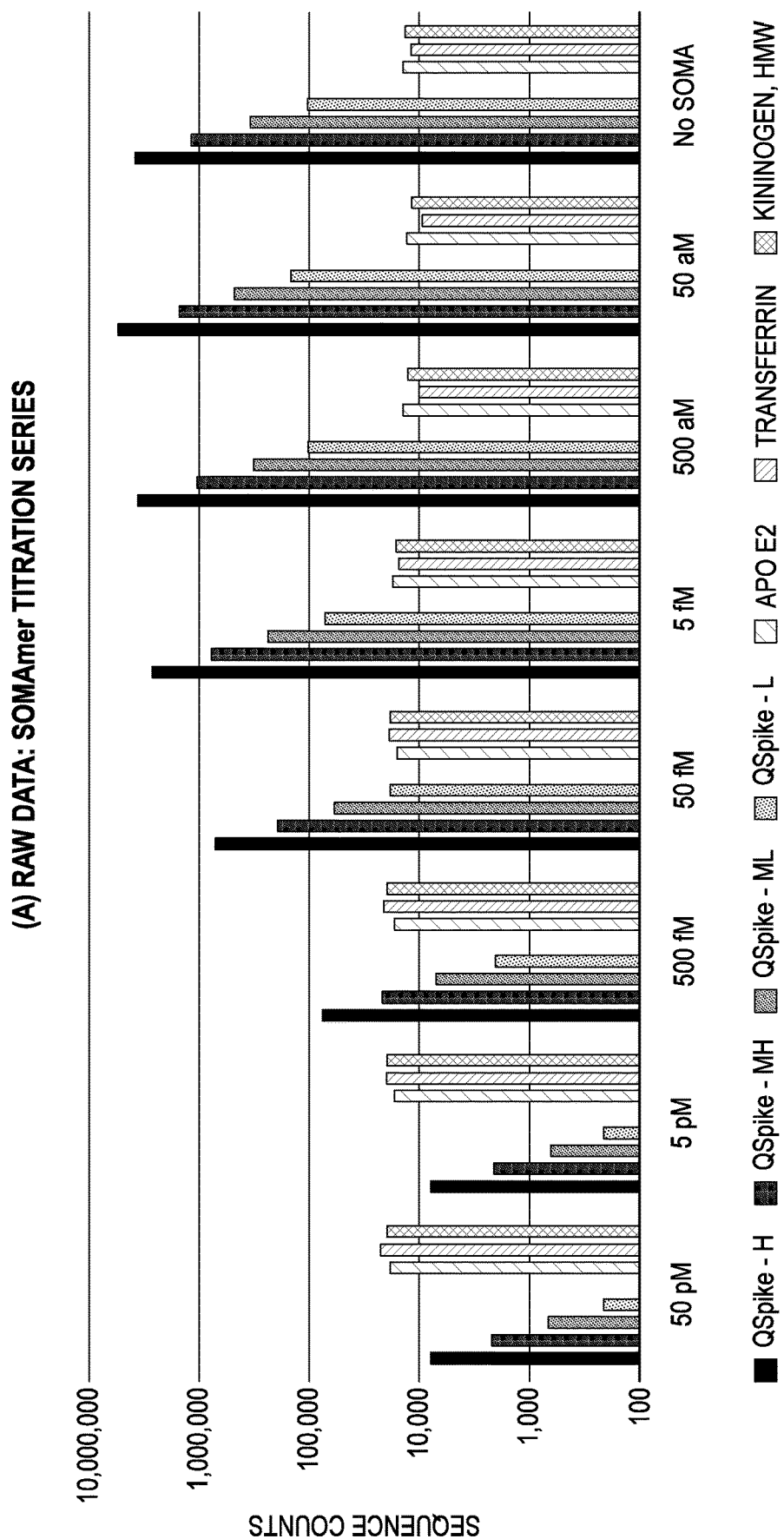
FIG. 9 is a graph depicting in histogram form the raw results of a three-analyte SOMAmer assay of eight separate samples with different analyte concentrations, where four different qSpike reporters were added to each sample, in accordance with aspects of the present teachings.
Figure 10:
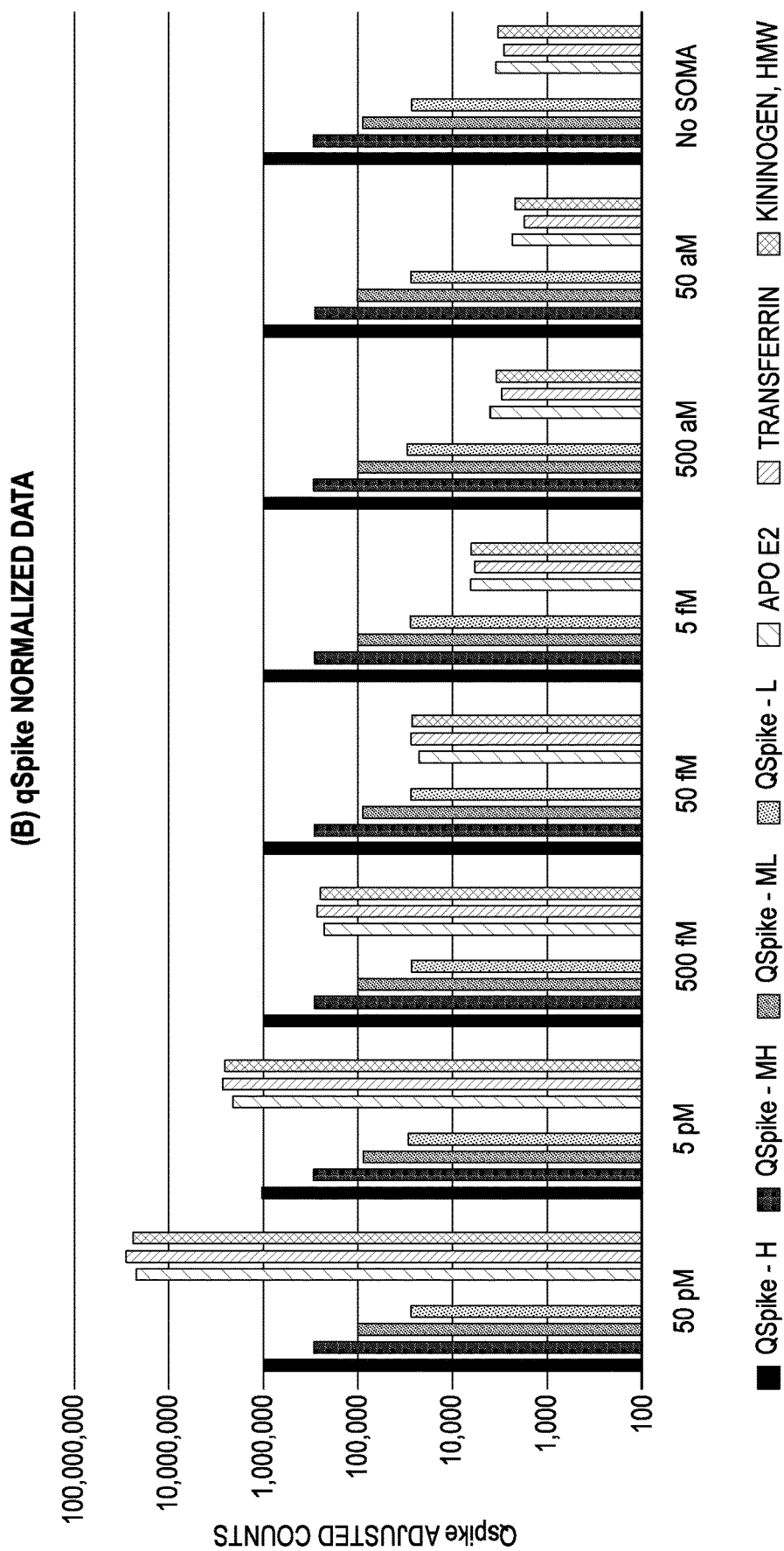
FIG. 10 is a graph depicting in histogram form the normalized results of the assay of FIG. 9, in accordance with aspects of the present teachings.

FIGS. 9-10 are histograms respectively depicting the raw and qSpike-adjusted results of such an assay, where the legend references have the following meanings:
QSpike—H=high concentration qSpike reporter
QSpike—MH=medium-high concentration qSpike reporter
QSpike—ML=medium-low concentration qSpike reporter
QSpike—L=low concentration qSpike reporter
Apo E2, Transferrin, and Kininogen HMW=SOMAmer analytes In the assay represented by FIGS. 9-10, the three SOMAmers Apo E2, Transferrin, and Kininogen HMW were titrated in buffer at concentrations ranging from 50 pM-50 aM, and measured in the NGS HC-assay. Each measurement point is a separate sample in which all three SOMAmer analytes are sequenced together, and the qSpike is added at the same concentrations to all samples.

In graph (A) of FIG. 9, the qSpike exhibits compensatory changes due to the analyte dose response signal changes. The NGS assay signals (read counts) are compared relative to the known spike, and scale factors are generated. In graph (B) of FIG. 10, the NGS counts have been scaled so the spike is even for all samples, which rebuilds the actual SOMAmer dose response for the three SOMAmers measured in the assay.

Figure 11:
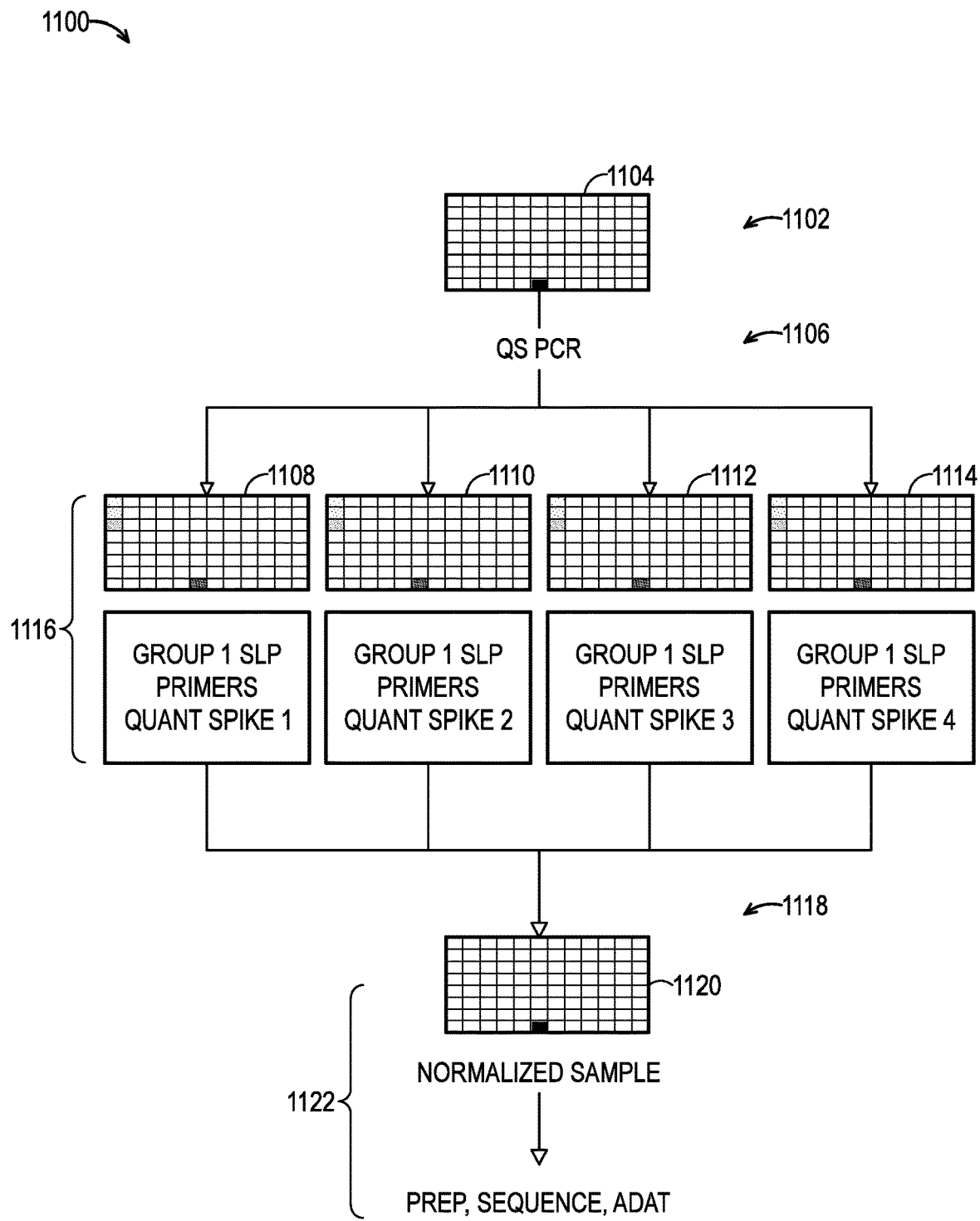
FIG. 11 is a flow diagram depicting some of the steps and byproducts of an exemplary next-generation sequencing assay involving four PCR groups and qSpike control reporters added to each group, in accordance with aspects of the present teachings.

The use of qSpike reporters to compensate for finite read counting can be incorporated into any of the next-generation sequencing assays described previously. For example, FIG. 11 depicts some of the steps and byproducts of an exemplary NGS assay, generally indicated at 1100, which involves four PCR groups as well as the addition of qSpike reporters to each group. Accordingly, the steps of assay 1100 can be incorporated into any NGS assay that uses multiple PCR groups, such as assays 500 and 600 depicted in FIGS. 5-6.

At step 1102, an eluate 1104 containing SOMAmers already hybridized with probes, captured to beads, washed, and eluted is provided. Eluate 1104 should therefore be viewed as generally similar to the eluate resulting, for example, from step 510 of assay 500 depicted in FIG. 5, or resulting from step 626 of assay 600 depicted in FIG. 6.

At step 1106, eluate 1104 is divided into four equal parts or aliquots 1108, 1110, 1112, and 1114. Each aliquot may optionally be diluted to any desired degree at this stage, to normalize the expected concentration of SOMAmer ID sequences to be amplified in the next step.

At step 1116, the separate eluates resulting from step 1106 are prepared for next-generation sequencing (NGS), including PCR amplification of the reporter regions. As in assays 500 and 600, different sets of primers and associated reporter regions are amplified in each separate eluate, resulting of amplification of a subset of SOMAmer ID sequences in each eluate. In this case, however, a different qSpike reporter is also added to each eluate prior to PCR amplification, at a known concentration.

At step 1118, the separate solutions containing amplified SOMAmer ID sequences and qSpike reporters in each aliquot are recombined into a single eluate solution 1120. In some cases, the separate solutions may be recombined at different volumes, resulting in a desired degree of dilution of relatively abundant SOMAmer ID sequences, and a normalized combined solution with less overall variation in SOMAmer ID concentrations, which may be analyzed with relatively fewer reads.

At step 1122, solution 1120 is further prepared for NGS, sequenced, and the results are written to a data file and analyzed. Preparation of the amplified eluates may include attaching adapter sequences and/or barcode sequences for demultiplexing to the amplified reporter sequences of the tri-molecular compounds. The prepared solution is then sequenced using NGS techniques, after which the data obtained from sequencing may be analyzed or otherwise processed to determine the concentrations of target analytes in the original biological samples. Due to the use of qSpike reporters, the analysis can include scaling or renormalizing the data to bring the qSpike concentrations back to their known levels, thereby compensating for possible counting errors due to finite sequencing reads.

E. Determining SOMAmer-Probe Stability

As discussed previously, according to aspects of the present teachings, hybridization regions $H_1$ and $H_2$ are configured to bind to the respective complementary portions of a corresponding SOMAmer, and may be designed to have similar or intentionally different melting temperatures ($T_m$) to achieve uniform hybridization under a given set of assay conditions. As discussed in this section, in some cases the melting temperatures for the hybridization regions may be estimated computationally, using experimentally determined melting profiles for SOMAmer-probe pairs.

1. Background

The most widely employed method for predicting nucleic acid duplex stability is known as the nearest-neighbor model. The nearest-neighbor model assumes that the thermodynamic properties for helix formation depend primarily on the identity of neighboring base pairs in the duplex. This model has been widely adapted for use in predicting stability of duplex formation for primer design needed in PCR and other applications where oligonucleotide duplex formation is key. For NGS assays according to the present teachings (i.e., involving SOMAmers), it is desirable to extend this method for accurate predictions of duplex stability comprised of one strand containing modified DNA bases of one kind, and a second strand with native DNA bases.

Absorbance versus temperature profiles (melting curves), measured with UV-vis spectrophotometers, have traditionally been used to study the stability of DNA secondary structure. The hybridization is typically performed in 1.0 M NaCl, 10 mM sodium cacodylate, and 0.5 mM $Na_2EDTA$ buffer at pH 7. The oligonucleotide concentration is varied over 100-fold range and the thermodynamic parameters are obtained from plots of the inverse melting temperature ($T_M^{-1}$) versus the natural log of the total DNA concentration and fit to $$T_M^{-1} = \left(\frac{R}{\Delta H °}\right)\ln\frac{C_T}{4} + \left(\frac{\Delta S °}{\Delta H °}\right)$$

Alternatively, $\Delta H°$ and $\Delta S°$ can be obtained from individual fits to the melting curves and averaged over the different concentrations. Both methods are essentially a van't Hoff analysis of the data. Thermodynamic data obtained from these two analysis methods typically agree within 10%. This section will exclusively use the latter method—individual fits to melting curve profiles—for extracting thermodynamic parameters for predicting mixed duplex stability. In addition, the buffer composition in which the thermal melting profiles are obtained will match the composition from a typical SOMAmer-containing assay readout.

According to aspects of the present teachings, an extension of the nearest-neighbor model is developed for SOMAmers containing the three most common modified bases, Nap-dU, 2-Nap-dU, and Benzyl-dU. As discussed below, melting profiles were obtained experimentally using fluorescence measurements for over 400 SOMAmer-probe pairs. These data were used to define the necessary nearest-neighbor parameters required for predicting SOMAmer-probe stabilities under assay readout conditions.

2. Duplex Formation to Model SOMAmer-Probe Binding

SOMAmer-probe duplex formation follows the following process:

$$S + \rho \rightleftharpoons S{:}\rho$$

where S is the SOMAmer, $\rho$ is the hybridization probe and $S{:}\rho$ is the duplex. Defining $C_T$ as the total concentration of initial DNA:

$$C_T = [S] + [\rho],$$

the following equations follow from stoichiometry, assuming the initial concentrations of SOMAmer and probe are equal:

$$[S] = [p] = (1-\alpha)\frac{C_T}{2}$$

$$[S{:}p] = \alpha \frac{C_T}{2}$$

where $\alpha$ is the molar fraction of duplex. The equilibrium constant for duplex formation is $$K = \frac{[S{:}p]}{[S][p]} = e^{-(\Delta H - T\Delta S)/RT}$$

where $\Delta H$ and $\Delta S$ are the enthalpy and entropy of duplex formation, T is the absolute temperature (K) and R is the gas constant (1.9872 cal/K·mol). Substituting the equations for concentrations gives $$K = \frac{\alpha \frac{C_T}{2}}{\left((1-\alpha)\frac{C_T}{2}\right)^2} = e^{-(\Delta H - T\Delta S)/RT}$$

By definition, $T_M$ corresponds to the temperature at which equal fractions of duplex and non-duplex occur, i.e., $\alpha = \frac{1}{2}$ giving the following expression for the melting temperature:

$$T_M = \frac{\Delta H}{\Delta S + R\ln\left(\frac{C_T}{4}\right)}$$

3. SOMAmer Melt Model

SOMAmers with internal structure can also be regarded as a simple two-state model as follows:

$$S \rightleftharpoons U$$

where S and U are the structured and unstructured SOMAmer. Defining $C_T$ as the total concentration of initial DNA, $$C_T = [S] + [U]$$

the following equations follow from stoichiometry $$[S] = \beta \frac{C_T}{2}$$

$$[U] = (1-\beta)\frac{C_T}{2}$$

where $\beta$ is the molar fraction of structured SOMAmer. The equilibrium constant for structured SOMAmer is then $$K = \frac{[S]}{[U]} = e^{-(\Delta H - T\Delta S)/RT}$$

where $\Delta H$ and $\Delta S$ are the enthalpy and entropy of structure formation, T is the absolute temperature (K) and R is the gas constant (1.9872 cal/K·mol). Substituting the equations for concentrations in terms of the molar fraction of structured SOMAmer gives $$K = \frac{\beta}{(1-\beta)} = e^{-(\Delta H - T\Delta S)/RT}$$

Again, by definition, the $T_M$ corresponds to the temperature at which equal fractions of structured and non-nonstructured SOMAmer occur, i.e., $$\beta = \frac{1}{2}$$

giving the following:

$$T_M = \frac{\Delta H}{\Delta S}$$

There is no entropic contribution from the concentration of SOMAmer, because this is a unimolecular reaction and all reactions are independent under reasonably dilute conditions. The simplest model is to assume independent processes for SOMAmer melting followed by primer melting or vice versa. There is no way of knowing a priori which of the two transitions is due to SOMAmer structure melting or hybridization primer melting without additional experiments, such as independent SOMAmer melts. The primer melt is most likely the higher free-energy data since it corresponds to better than 16 base pairs melting.

4. Experimental Determination of Thermodynamics of Melting

Fluorescent intensity versus temperature profiles (melting curves) were measured with a fluorescent dye, SYBR Green I. The fluorescent intensity of SYBR Green I increases 100-fold when bound to double stranded DNA compared to single stranded DNA, therefore the fluorescent intensity decreases as the SOMAmer-Probe duplex structure melts.

Thermal melting was performed in a buffer with components defined by the SOMAscan assay eluate, in this case 100 mM Tris pH 8.0, 200 mM NaCl and 0.9 M perchlorate. Perchlorate is known to decrease DNA duplex stability. All thermal melts were obtained at a single concentration for both SOMAmer and probe of 100 pM in 120 µL ($8.3 \times 10^{-7}$ M). Therefore, all thermodynamic parameters were obtained from single fits to the individual thermal melting profiles. Melting profiles that exhibited more complex behavior than that expected for a two-state model were excluded from analysis. A total of 4 plates each for $H_1$ and $H_2$ probes were measured. These 800 melting profiles were assessed for producing data consistent with an assumed two-state model of duplex formation. Out of these 800 profiles, a total of 408 melting profiles for SOMAmers containing three different modified nucleotides, Nap-dU, 2-Nap-dU, and Benzyl-dU were used in this analysis.

a. Single-phase Model Fit

Figure 12:
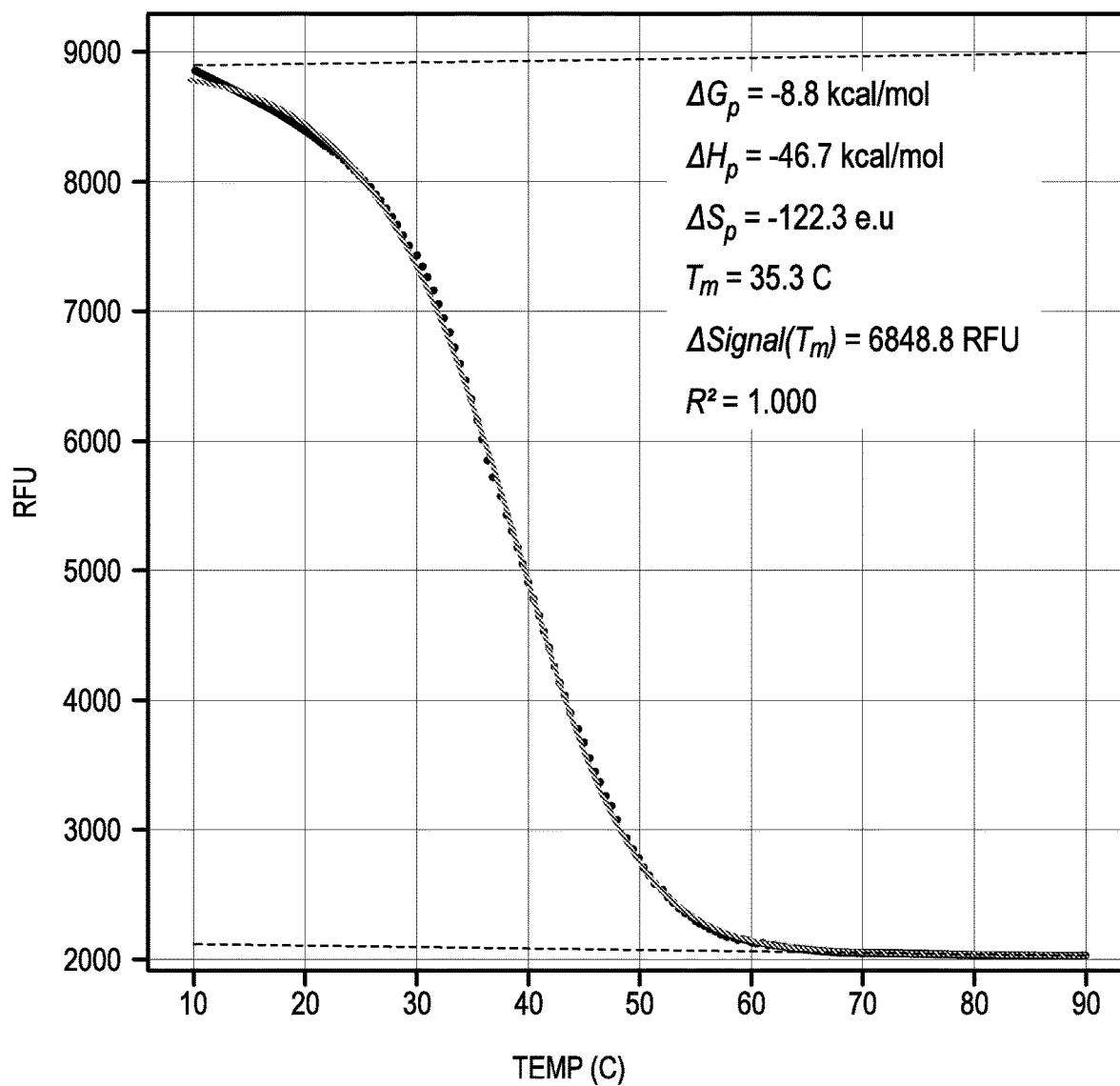
FIG. 12 is a graph of relative fluorescent units (RFU) versus temperature, depicting experimentally obtained single phase thermal melting data for a SOMAmer-probe duplex, overlaid by a two-state theoretical model curve fit, in accordance with aspects of the present teachings.

FIG. 12 shows data for a typical thermal melt for SOMAmer-probe duplex, with fluorescence measured in RFU on the vertical axis, and temperature on the horizontal axis, overlaid by a two-state model fit as follows. First, the high and low temperature baselines are fit to the data using the first and last 15 data points. The low temperature baseline corresponds to double stranded material, and the high temperature baseline that of single stranded material, denoted as $$bl_{ds} = b_{ds} + m_{ds}T$$

$$bl_{ss} = b_{ss} + m_{ss}T.$$

For a given value of $\Delta H$ and $\Delta S$, the fraction of duplex as a function of temperature is obtained by first computing K and then $\sigma$ $$\alpha = b - \sqrt{b^2 - 1}$$

where $$b = 1 + 1/(KC_T).$$

The profile of the thermal melt, RFU(T), is computed from $$RFU(T) = \alpha bl_{ds} + (1-\alpha)bl_{ss}.$$

A nonlinear regression is used to find the optimal values for the six free parameters, $b_{ds}$, $m_{ds}$, $b_{ss}$, $m_{ss}$, $\Delta H$, and $\Delta S$. Initial estimates for the single- and double-stranded baselines are obtained as described above, and the initial values for $\Delta H$ and $\Delta S$ are −200 kcal/mol and −0.6 kcal/mol·K. The model fit for the data in FIG. 12 are displayed as the solid red curve in FIG. 12. The subscript 'p' denotes SOMAmer-probe thermodynamics. The model fit the data extremely well.

b. Biphasic Model Fits

Figure 13:
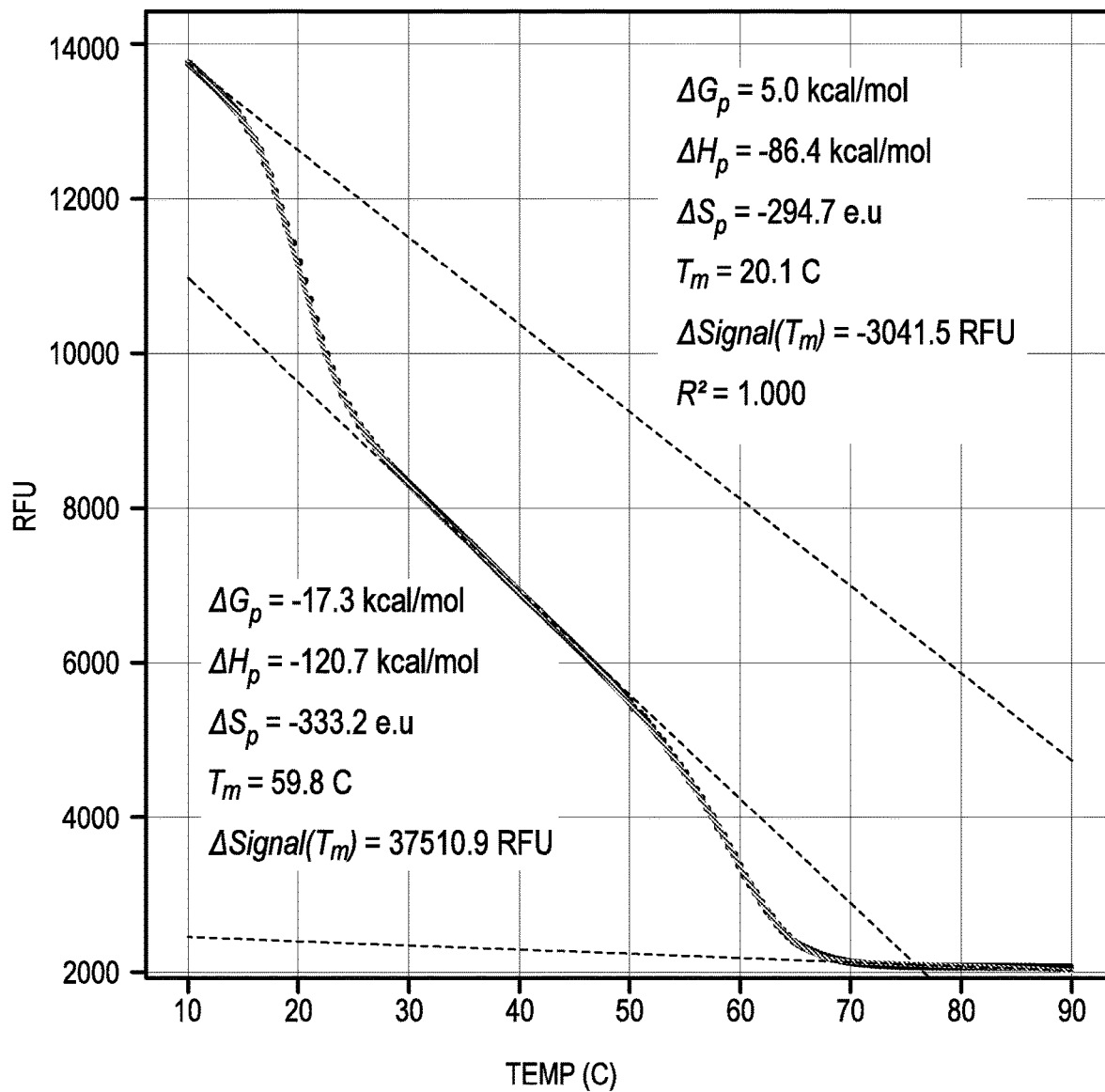
FIG. 13 is a graph of relative fluorescent units (RFU) versus temperature, depicting experimentally obtained biphasic thermal melting data for a SOMAmer-probe duplex, overlaid by a biphasic theoretical model curve fit, in accordance with aspects of the present teachings.

Often, the data exhibit more complex melting behavior most likely due to first melting of SOMAmer internal structure followed by melting of the SOMAmer-probe duplex. FIG. 13 illustrates data representing typical biphasic behavior, again overlaid by a theoretical model fit indicated by the solid red line. Two clear transitions occur in the data, presumably the first is melting of internal SOMAmer structure followed by duplex melting of the SOMAmer-probe. The two transitions are assumed to be independent. To fit a bi-phasic model, three baselines are required. The first corresponds to the temperature dependence on the internal SOMAmer structure, the second is that for the double-stranded SOMAmer-probe, and the third is for the combined single-stranded material. The latter two are the same as those baselines described above. The former is denoted as $$bl_{int} = b_{int} + m_{int}T$$

where it is assumed that the fluorescence is additive so represents an increase in fluorescence over that of the double-stranded SOMAmer-probe complex. At low temperature, both the internal structure in the SOMAmer and the SOMAmer-probe duplex exist, so the net fluorescence is assumed to be a sum of the independent structures. Denoting the mole fraction of SOMAmer internal structure as $\beta$ and that for SOMAmer-probe duplex as $\alpha$, the thermal melt profile will be given by $$RFU(T) = \beta(bl_{int} - bl_{ds}) + \alpha bl_{ds} + (1-\alpha)bl_{ss}.$$

At low temperature, both $\alpha$ and $\beta$ are one and the temperature dependence is given by $bl_{int}$. As the structure of the SOMAmer melts, the fluorescence is due entirely to the baseline of the double-stranded duplex. As in the case of the single phase, the biphasic model fits the data extremely well.

5. Nearest Neighbor Model

Once the experimental data have been fit to an appropriate model (e.g., single phase or biphasic, as discussed above), and the individual thermodynamic parameters have been compiled, the parameters for the nearest neighbor model may be obtained from the data. The change in free energy is approximated by:

$$\Delta G_i(\text{total}) = \sum_j n_{ij} \Delta G_j + \Delta G(init)$$

where the i subscript denotes a SOMAmer-probe duplex, $\Delta G_j$ are the free energies for the nearest-neighbor stacking interactions, $n_{ij}$ are the number of occurrences of the nearest neighbor j in duplex i, and $\Delta G(init)$ is the initiation free energy due to entropic considerations. The nearest neighbor interactions include the ten standard Watson-Crick nearest neighbor stacking interactions (e.g., $\Delta G_1 = \Delta G°_{37}$ (AA/TT), $\Delta G_2 = \Delta G°_{37}$ (AC/TG), etc.). The notation (AC/TG) means 5'-AC-3' Watson-Crick base-paired with 3'-TG-5'). In addition, each modified base introduces another seven modified nucleotide stacking interactions (e.g., $\Delta G_{11} = \Delta G°_{37}$ (XA/AT), $\Delta G_{12} = \Delta G°_{37}$ (XC/AG), etc.) where X denotes a modified T nucleotide that base-pairs with a standard A nucleotide. Analogous expressions for $\Delta H$ and $\Delta S$ hold.

For a set of d duplexes and n nearest neighbor interactions, a "stacking matrix" matrix N with dimensions d×n is constructed from the sequence data by computing the elements $n_{ij}$. The experimentally observed thermodynamic values $T_{total}$ are represented as a column vector of length d. The unknown nearest neighbor stacking interactions $I_{nn}$ are represented by a column vector of length n, and are obtained by solving the following overdetermined linear equation using the methods of ordinary least-squares regression:

$$NI_{nn} = T_{total}.$$

The parameters $I_{nn}$ minimize the Euclidean $l^2$ norm, $\|NI_{nn} - T_{total}\|$.

6. Exemplary Results

In an exemplary process according to the teachings above, thermal melts of duplexes containing three different modified nucleotides, Nap-dU, 2-Nap-dU, and Benzyl-dU, were used to extend the nearest-neighbor model parameters.

Python code has been developed for computing the thermodynamics and melting temperature based on these extended nearest-neighbor parameters.

The table below summarizes the 31 parameters required for the nearest-neighbor model, including 10 parameters for the standard four bases and 7 additional parameters for each modified base. The $\Delta H$ and $\Delta S$ values for each NN pair is included, as well as the total number of occurrences for each nearest-neighbor parameter in the data set. There are relatively few occurrences of (AT/TA) and (TA/AT) in the data, because these necessarily occur in the fixed regions only.

| NN Pair | $\Delta H$ (kcal/mol) | $\Delta S$ (e.u.) | Occurrences |
|---|---|---|---|
| AA/TT | −6.1 | −17.0 | 670 |
| AC/TG | −15.0 | −41.2 | 650 |
| AG/TC | −3.9 | −9.5 | 664 |
| AT/TA | −10.5 | −26.6 | 19 |
| CA/GT | −0.7 | −1.5 | 769 |
| CC/GG | −6.9 | −17.7 | 929 |
| CG/GC | −3.9 | −9.4 | 364 |
| GA/CT | −8.4 | −23.9 | 679 |
| GC/CG | −15.6 | −42.1 | 394 |
| TA/AT | 3.1 | 7.9 | 12 |
| XA/AT | −5.7 | −18.6 | 561 |
| XC/AG | −15.9 | −47.2 | 383 |
| XG/AC | −10.7 | −31.5 | 459 |
| XX/AA | 0.2 | −0.7 | 627 |
| AX/TA | 5.5 | 16.7 | 521 |
| CX/GA | 9.7 | 29.5 | 390 |
| GX/CA | 4.5 | 13.6 | 484 |
| YA/AT | 0.4 | 0.4 | 112 |
| YC/AG | −8.7 | −26.1 | 100 |
| YG/AC | −12.9 | −37.1 | 119 |
| YY/AA | 3.0 | 7.5 | 172 |
| AY/TA | −2.3 | −7.2 | 123 |
| CY/GA | 6.2 | 18.1 | 98 |
| GY/CA | 1.7 | 5.2 | 112 |
| ZA/AT | −9.4 | −26.6 | 85 |
| ZC/AG | −14.9 | −41.9 | 46 |
| ZG/AC | −9.9 | −26.3 | 92 |
| ZZ/AA | −3.1 | −8.7 | 128 |
| AZ/TA | −10.8 | −31.8 | 71 |
| CZ/GA | 1.4 | 4.4 | 67 |
| GZ/CA | −14.0 | −40.0 | 77 |

Using the parameters in the table above, estimated melting temperatures $T_m$ may be determined computationally for duplexes containing the modified nucleotide bases Nap-dU, 2-Nap-dU, and Benzyl-dU. A similar procedure may be used to compute estimated melting temperature for any other SOMAmer-containing duplexes. According to aspects of the present teachings, these melting temperatures may then be used to determine where to divide the hybridization complement to the SOMAmer, i.e., the dividing point between the first and second hybridization regions $H_1$ and $H_2$ (and thus between first and second probes 104 and 106) of tri-molecular compounds such as compound 100 depicted in FIG. 1.

F. Illustrative Combinations and Additional Examples

This section describes additional aspects and features of systems and method for detecting and quantifying target molecules in a biological sample according to aspects of the present teachings, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A. A system for quantifying the abundances of target proteins in a biological sample, comprising a plurality of aptamers each configured to bind to a specific target protein upon exposure of a biological sample containing target proteins to the aptamers, thereby forming an aptamer-containing eluate; a plurality of capture probes each configured to hybridize to a particular aptamer, wherein the plurality of capture probes includes first capture probes having a portion hybridized to a first portion of the respective aptamer, and second capture probes having a portion hybridized to a second portion of the respective aptamer, a DNA primer region, and an aptamer ID sequence corresponding to the aptamer; means for forming a plurality of tri-molecular complexes by exposing the aptamers in the eluate to the capture probes; and means for sequencing the aptamer ID sequences, thereby determining the abundances of the target proteins in the biological sample.

B. A system for quantifying the abundances of two or more species of target proteins in a biological sample, comprising a plurality of aptamers each configured to capture a specific protein in the sample, thereby forming an aptamer-containing eluate upon isolation of the aptamers that captured one of the target proteins in the biological sample; a plurality of first probes each hybridized to a corresponding first portion of a particular aptamer; a plurality of second probes each hybridized to a corresponding second portion of the particular aptamer, each second probe including at least one DNA primer region, and an aptamer ID sequence corresponding to the particular aptamer; means for sequencing the aptamer ID sequences; and based on the sequenced aptamer ID sequences, means for quantifying the abundances of the target proteins.

C. A system for detecting a target protein in a biological sample, comprising a plurality of aptamers each configured to capture a specific protein; a plurality of first probes each including a portion hybridized to a corresponding first portion of one of the aptamers that captured a target protein; a plurality of second probes each including a portion hybridized to a corresponding second portion of one of the aptamers that captured a target protein, at least one DNA primer region, and an aptamer ID sequence corresponding to the aptamer that captured the target protein; means for amplifying the aptamer ID sequence; and means for sequencing the aptamer ID sequence to identify the aptamer ID sequence thereby identifying the aptamer that captured the target protein and the target protein.

D. The system of any of the preceding paragraphs, further comprising means for normalizing compensatory read counts across samples.

E. The system of any of the preceding paragraphs, further comprising means for dynamic range compression of abundances of aptamers and/or aptamer ID sequences before sequencing and counting.

Advantages, Features, and Benefits

The different embodiments and examples of the method and systems described herein for detecting and quantifying the presence of target molecules in a biological sample provide several advantages over previously known solutions. For example, illustrative embodiments and examples described herein allow aptamer-based protein detection to be quantified using next-generation sequencing, by simplifying the sequencing targets from aptamers to aptamer identification sequences.

Additionally, and among other benefits, illustrative embodiments and examples described herein allow accurate target molecule detection across many orders of magnitude of abundances, by splitting the assay eluate into a plurality of dilution groups at one or more stages of the assay, and then recombining before next-generation sequencing.

Additionally, and among other benefits, illustrative embodiments and examples described herein allow for correction of errors resulting from finite sequencing reads, by adding quantitative spike reporters to the assay eluate to normalize compensatory read counts across samples.

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A method for quantifying the abundances of target proteins in a biological sample, comprising:
   capturing the target proteins by exposing the biological sample to a plurality of aptamers each configured to bind to a specific protein;
   isolating the aptamers that captured one of the target proteins in an aptamer-containing eluate;
   forming a plurality of tri-molecular complexes by exposing the aptamers in the eluate to a plurality of capture probes each configured to hybridize to a particular aptamer, each tri-molecular complex including:
   one of the aptamers from the eluate,
   a first capture probe including a portion hybridized to a first portion of the aptamer, and
   a second capture probe including a portion hybridized to a second portion of the aptamer, a DNA primer region, and an aptamer ID sequence corresponding to the aptamer;
   separating the tri-molecular complexes from capture probes not bound to aptamers;
   dissociating the capture probes in the tri-molecular complexes from the corresponding aptamers;
   amplifying the aptamer ID sequences of the dissociated second capture probes;
   sequencing the amplified aptamer ID sequences of the dissociated second capture probes via next-generation sequencing; and
   based on data obtained by sequencing the aptamer ID sequences, determining the abundances of the target proteins in the biological sample.

2. The method of claim 1, wherein the aptamers are have a rate of protein-aptamer dissociation $t_{1/2}$ between 30 and 240 minutes.

3. The method of claim 1, further comprising dividing the aptamer-containing eluate into two or more groups prior to forming the tri-molecular complexes, and wherein the aptamers in each aptamer-containing eluate group are exposed to a different set of capture probes.

4. The method of claim 1, further comprising dividing the dissociated capture probes into a plurality of aliquots prior to amplifying the aptamer ID sequences of the dissociated second capture probes, and wherein amplifying the aptamer ID sequences includes amplifying a different subset of aptamer ID sequences in each aliquot.

5. The method of claim 4, further comprising diluting at least one of the aliquots before amplifying the aptamer ID sequences of the dissociated second capture probes.

6. The method of claim 4, further comprising adding a quantitative spike reporter to each aliquot before amplifying the aptamer ID sequences of the dissociated second capture probes.

7. The method of claim 6, further comprising recombining the aliquots prior to sequencing the amplified aptamer ID sequences of the dissociated second capture probes.

8. The method of claim 1, wherein the aptamers have chemically modified nucleotides.

9. A method for quantifying the abundances of two or more species of target proteins in a biological sample, comprising:
   capturing the target proteins by exposing the biological sample to a plurality of aptamers each configured to capture a specific protein;
   forming an aptamer-containing eluate by isolating the aptamers that captured one of the target proteins in the biological sample;
   forming a plurality of tri-molecular complexes, each including:
   a particular aptamer present in the aptamer-containing eluate,
   a first probe hybridized to a corresponding first portion of the particular aptamer, and
   a second probe including a portion hybridized to a corresponding second portion of the particular aptamer, at least one DNA primer region, and an aptamer ID sequence corresponding to the particular aptamer;
   amplifying the aptamer ID sequences of the second probes;
   sequencing the amplified aptamer ID sequences of the second probes; and
   based on the sequenced aptamer ID sequences, quantifying the abundances of the target proteins.

10. The method of claim 9, wherein the aptamers have a rate of protein-aptamer dissociation $t_{1/2}$ between 30 and 240 minutes.

11. The method of claim 9, further comprising dividing the aptamer-containing eluate into two or more dilution groups prior to forming the tri-molecular complexes, and wherein each dilution group contains a distinct set of capture probes.

12. The method of claim 9, further comprising dividing the capture probes into a plurality of aliquots prior to amplifying the aptamer ID sequences of the second probes, wherein at least one of the aliquots is diluted, and wherein amplifying the aptamer ID sequences of the second probes includes amplifying a different subset of aptamer ID sequences in each aliquot.

13. The method of claim 12, further comprising adding a quantitative spike reporter to each aliquot before amplifying the aptamer ID sequences of the second probes.

14. The method of claim 13, further comprising recombining the aliquots prior to sequencing the amplified aptamer ID sequences of the second probes.

15. The method of claim 9, wherein sequencing the amplified aptamer ID sequences of the second probes is accomplished via next generation sequencing.

16. The method of claim 9, wherein the aptamers have chemically modified nucleotides.

17. A method for detecting a target protein in a biological sample, comprising:
   capturing the target protein with an aptamer by combining the biological sample with a plurality of aptamers each configured to capture a specific protein;
   forming a tri-molecular complex including:
   the aptamer that captured the target protein,
   a first probe including a portion hybridized to a corresponding first portion of the aptamer that captured the target protein, and
   a second probe including a portion hybridized to a corresponding second portion of the aptamer that captured the target protein, at least one DNA primer region, and an aptamer ID sequence corresponding to the aptamer that captured the target protein;
   amplifying the aptamer ID sequence of the second probe; and
   sequencing the amplified aptamer ID sequence of the second probe to identify the aptamer ID sequence of the second probe, thereby identifying the aptamer that captured the target protein and identifying the target protein.

18. The method of claim 17, further comprising forming the first and second probes by determining a target region on the aptamer, and then determining a boundary for dividing a complement of the target region into the first and second probes.

19. The method of claim 18, wherein determining the boundary is based on achieving desired melting temperatures for the hybridized portions of the first and second probes.

20. The method of claim 19, further comprising determining the melting temperature of the complement of the target region computationally, and then stepping through boundary changes between the hybridized portions of the first and second probes until the desired melting temperatures of the hybridized portions are achieved.

21. The method of claim 19, wherein sequencing the amplified aptamer ID sequence of the second probe is accomplished via next generation sequencing.

22. The method of claim 17, further comprising dissociating the second probe from the aptamer before amplifying the aptamer ID sequence of the second probe.

* * * * *

UNITED STATES PATENT AND TRADEMARK OFFICE
CERTIFICATE OF CORRECTION

PATENT NO. : 11,965,880 B2
APPLICATION NO. : 18/148350
DATED : April 23, 2024
INVENTOR(S) : Dom Zichi et al.

It is certified that error appears in the above-identified patent and that said Letters Patent is hereby corrected as shown below:

In the Claims

Column 28, Line 7, the text "The method of claim 1, wherein the aptamers are have" should read --The method of claim 1, wherein the aptamers have--.

Signed and Sealed this
Twenty-first Day of May, 2024

Katherine Kelly Vidal
*Director of the United States Patent and Trademark Office*